US012728036B2

(12) United States Patent
Yick et al.

(10) Patent No.: US 12,728,036 B2
(45) Date of Patent: Sep. 8, 2026

(54) INTRAOCULAR STENT

(71) Applicant: NEW WORLD MEDICAL, INC., Rancho Cucamonga, CA (US)

(72) Inventors: Lee C. Yick, San Gabriel, CA (US); Eric Porteous, Corona, CA (US); Derek Ng, Long Beach, CA (US); Bobby Xiong, Orange, CA (US); Malik Y. Kahook, Denver, CO (US); John Koontz, Chino, CA (US); Vijay Balan, Torrance, CA (US)

(73) Assignee: NEW WORLD MEDICAL, INC., Rancho Cucamonga, CA (US)

( * ) Notice: Subject to any disclaimer, the term of this patent is extended or adjusted under 35 U.S.C. 154(b) by 225 days.

(21) Appl. No.: 18/574,847

(22) PCT Filed: Jul. 5, 2022

(86) PCT No.: PCT/US2022/036126
§ 371 (c)(1),
(2) Date: Dec. 28, 2023

(87) PCT Pub. No.: WO2023/287611
PCT Pub. Date: Jan. 19, 2023

(65) Prior Publication Data

US 2024/0350315 A1 Oct. 24, 2024

Related U.S. Application Data

(60) Provisional application No. 63/333,386, filed on Apr. 21, 2022, provisional application No. 63/277,353,
(Continued)

(51) Int. Cl.
*A61F 9/007* (2006.01)
*A61M 27/00* (2006.01)

(52) U.S. Cl.
CPC .. *A61F 9/00781* (2013.01); *A61F 2220/0016* (2013.01); *A61F 2250/0065* (2013.01); *A61M 27/002* (2013.01)

(58) Field of Classification Search
CPC .......... A61F 9/00781; A61F 2220/0016; A61F 2250/0065; A61F 2220/0008; A61F 2220/0033; A61M 27/002
See application file for complete search history.

(56) References Cited

U.S. PATENT DOCUMENTS 7,488,303 B1 2/2009 Haffner et al.
2004/0102729 A1* 5/2004 Haffner .............. A61F 9/00781 623/1.11

(Continued)

FOREIGN PATENT DOCUMENTS

JP 2005512607 A 5/2005
JP 2020162921 A 10/2020

OTHER PUBLICATIONS

International Search Report and Written Opinion for Application No. PCT/US2022/036126, dated Oct. 21, 2022, 12 pages.

(Continued)

*Primary Examiner* — Susan S Su
(74) *Attorney, Agent, or Firm* — MASCHOFF BRENNAN

(57) ABSTRACT

Intraocular stents are provided. An intraocular stent (20) includes a piercing end (40) for penetration into portions of the eye without requiring a surgical incision by a separate cutting device. A first retention member (50) stabilizes the intraocular stent (20) against the anterior wall of the canal of Schlemm. A second retention member (60) stabilizes the intraocular stent within the trabecular meshwork. A fluid inlet end (72) is configured to be disposed within the anterior chamber. In use. aqueous humor fluid flows into the fluid inlet end (72) through a central lumen (70) and/or drainage (Continued)

tubes (80) and out into the canal of Schlemm. Stack configurations of intraocular stents and insertion devices are also provided.

16 Claims, 26 Drawing Sheets

Related U.S. Application Data filed on Nov. 9, 2021, provisional application No. 63/222,691, filed on Jul. 16, 2021.

(56) References Cited

U.S. PATENT DOCUMENTS

2005/0266047 A1 12/2005 Tu et al.
2010/0087774 A1* 4/2010 Haffner .............. A61F 9/00781 604/8
2010/0274259 A1* 10/2010 Yaron ................ A61M 27/002 604/8
2013/0090534 A1* 4/2013 Burns .................... G16H 10/60 600/398
2014/0276332 A1* 9/2014 Crimaldi ............ A61F 9/00781 604/8
2016/0270958 A1* 9/2016 de Silva Curiel .. A61F 9/00781
2020/0345549 A1* 11/2020 Lu ........................ A61L 31/044

OTHER PUBLICATIONS

Extended European Search Report for Application No. 26160896.2, dated Mar. 20, 2026, 7 pages.
Japanese Office Action for Application No. 2024-502079, dated Apr. 17, 2026, 6 pages including translation.

* cited by examiner 620c
653c
654c
640c
650c
652c 620c
680
652c
646c
640c 620c
652c
648c
632
650c
640c
646c 720
744
742
780

720
780
742
744
746

720
766
732
748
744
746
743
750
742
740
760
730

INTRAOCULAR STENT

RELATED APPLICATIONS

This application claims the benefit of International Application No. PCT/US2022/036126, entitled "INTRAOCULAR STENT," filed on Jul. 5, 2022, which claims the benefit of and priority to U.S. Provisional Patent Application No. 63/222,691, filed Jul. 16, 2021, entitled "INTRAOCULAR STENT," U.S. Provisional Patent Application No. 63/277,353, filed Nov. 9, 2021, entitled "INTRAOCULAR STENT," and U.S. Provisional Patent Application No. 63/333,386, filed Apr. 21, 2022, entitled "INTRAOCULAR STENT, the entire contents of which are incorporated herein by reference.

TECHNICAL FIELD

The present disclosure generally relates to an intraocular stent, in particular an intraocular stent having a retention member.

BACKGROUND

Aqueous humor typically drains from the anterior chamber of the eye through the conventional aqueous outflow system of the eye via the trabecular meshwork, canal of Schlemm and more distal collector channels. Aqueous humor also drains through the uveoscleral outflow system. In some circumstances, reduced drainage of aqueous humor can increase intraocular pressure which can cause damage to the optic nerve and eventually blindness if left untreated. Intraocular aqueous humor drainage devices are used to provide increased drainage of aqueous humor from the anterior chamber and into the conventional aqueous humor outflow system. One approach is to use trabecular bypass implants that allow the aqueous humor to flow from the anterior chamber through the trabecular meshwork and out into the canal of Schlemm and subsequently to distal collector channels. Some typical shunts have a seat to rest against the trabecular meshwork and a side port perpendicular to a central lumen, which requires fluid flow to make a 90 degree turn within the shunt and also requires a surgical incision to be made in the trabecular meshwork in order to insert the shunt. Some typical medication delivery devices have a harpoon structure at a front end to allow the medication delivery device to be inserted through the trabecular meshwork and the wall of the canal of Schlemm without requiring a separate surgical incision from a cutting device. Accordingly, it is desirable to provide an intraocular stent having self-piercing and retention features for easy insertion and stable retention, and/or non-perpendicular fluid flow paths, in order to provide desirable fluid flow within the eye.

BRIEF DESCRIPTION OF THE DRAWINGS

The accompanying drawings, which are included to provide further understanding of the disclosure and are incorporated in and constitute a part of this specification, illustrate embodiments of the disclosure and together with the description serve to explain the principles of the disclosure.

DETAILED DESCRIPTION

Figure 2:
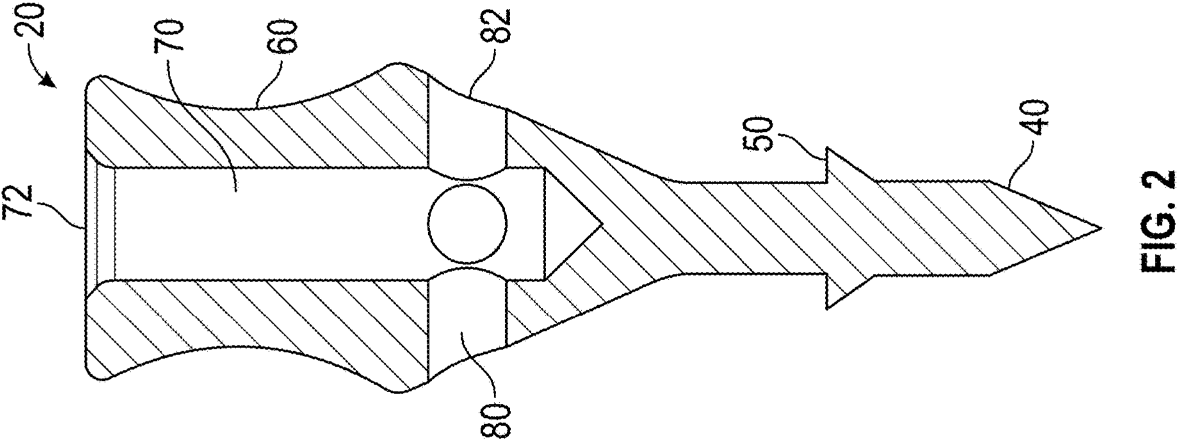
FIG. 2 depicts a cross-sectional front view of the intraocular stent of FIG. 1, according to aspects of the disclosure.

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions are provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the appended claims. Various aspects of the subject technology will now be disclosed according to particular but non-limiting examples. Various embodiments described in the present disclosure may be carried out in different ways and variations, and in accordance with a desired application or implementation.

While the occurrence of glaucoma and progression of disease are not tied to a specific IOP number, the only modifiable risk factor for glaucoma is that of intraocular pressure. The typical therapy is to decrease IOP and there are some general ranges that are considered desirable or less desirable. For example, average eye pressure ranges from 12-21 mm Hg. If IOP is too low (e.g., less than 6 mm of mercury), there is a danger of altered vision with swelling of the retina where the eye structure essentially decompensates and may result in blindness in that eye. On the other hand, if the IOP is consistently too high (e.g., more than 21 mm of mercury) or has spikes with fluctuating IOP, there is also a danger of optic nerve deterioration and blindness in the eye. Accordingly, an IOP between 10 mm and 18 mm of mercury is desirable to maintain optimal eye health. In many cases, treatments may aim for a decrease in IOP of 25-30% from baseline at the time of disease diagnosis or when disease advancement is noted. In some cases, even if the IOP is within the desirable range (e.g., 18 mm of mercury), it may be desirable to decrease the IOP to a lower value in the desirable range (e.g., 14 mm of mercury).

For eye diseases such as Glaucoma, for example, underdrainage of the aqueous humor increases the pressure into undesirable ranges. An intraocular drainage device (e.g., stent) may be used to relieve this pressure by providing drainage tubes that improve aqueous humor flow. Thus, it is very desirable that the drainage tubes maintain the desired aqueous humor flow. However, if the drainage tubes become partially or wholly blocked due to clotting or debris, the aqueous humor flow within the eye is reduced, thereby increasing the pressure. Also, if the stent does not maintain a stable position, the aqueous humor flow may be disrupted and/or deleterious medical effects may occur. Further, if the stent requires an incision by a separate cutting device in order to be inserted, a more invasive and/or more complex surgical procedure is required.

To overcome the insertion and stability issues with stents, as well as clotting and debris clogging issues with drainage tubes, the present disclosure provides for intraocular stents having a self-piercing front end (e.g., harpoon), a retention member that engages the anterior canal wall of the canal of Schlemm, a retention member that engages the trabecular meshwork and/or drainage tube paths or alignments that maximize fluid flow. The harpoon allows for insertion of the stent through the trabecular meshwork, the canal and the anterior canal wall of the canal of Schlemm without the need for a separate surgical incision. Here, the anterior wall of the canal of Schlemm is the part closest to the anterior surface of the eye, whereas the trabecular meshwork is more posterior, thus the posterior wall of the canal of Schlemm is just anterior to the trabecular meshwork and mostly adherent to the trabecular meshwork. The canal of Schlemm retention member prevents the harpoon from being retracted back through the canal wall, thus providing stability for the stent. The trabecular meshwork retention member engages with the trabecular meshwork, also providing stability for the stent. The drainage tube paths may be angled perpendicularly from a central lumen, angled non-perpendicularly from the central lumen, linear in parallel with the central lumen, linear but angled with respect to the central lumen, or linear through the stent without having a central lumen, many of which reduces clotting and debris buildup by providing less tortuous fluid flow paths. The central lumen and the drainage paths may be infused or coated with material (e.g., heparin) that enhances biologic compatibility and reduces clotting.

Figure 1:
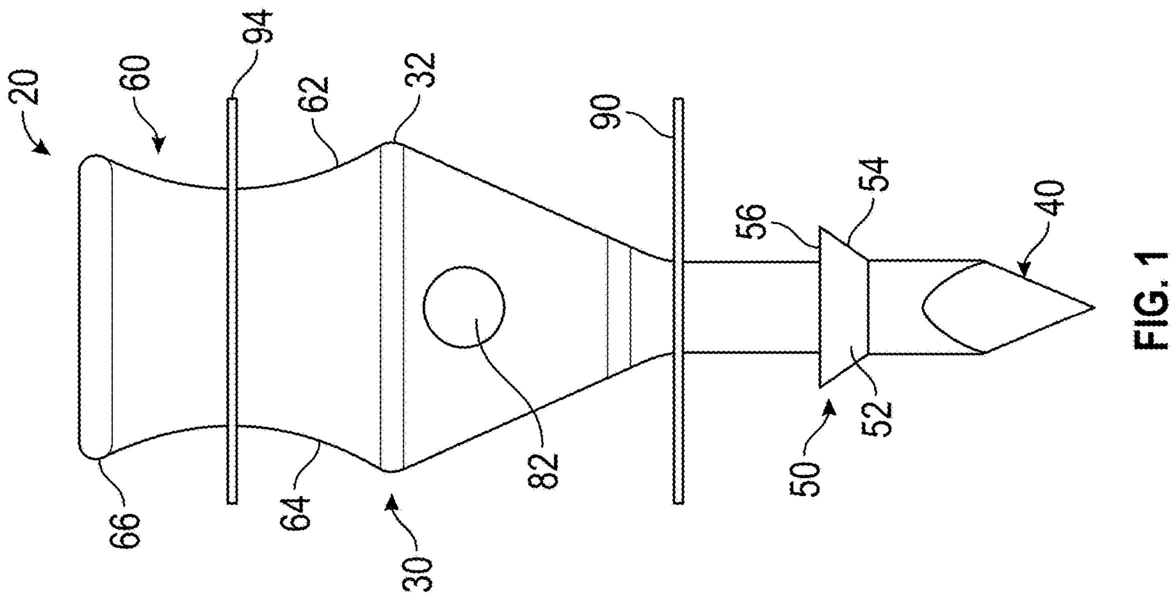
FIG. 1 depicts a front view of an intraocular stent, according to aspects of the disclosure.

Referring now in more detail to the drawings in which like reference numerals refer to like or corresponding elements among the several views, there is shown in FIGS. 1 and 2 an intraocular stent 20 having a housing 30, a piercing member 40 extending from the housing 30, a first retention member 50 disposed on the piercing member 40, a second retention member 60 disposed on the housing 30, a central lumen 70 axially disposed within the housing 30 and multiple drainage tubes 80 coupled with the central lumen 70 and disposed within the housing 30. As further shown in FIG. 1, the intraocular stent 20 is positioned relative to a canal wall 90 of the canal of Schlemm 92 of an eye and a trabecular meshwork 94 of the eye (see FIG. 53)

According to aspects of the disclosure, as shown in FIGS. 1 and 2, the piercing member 40 may be a pointed spike configured to penetrate both the trabecular meshwork 94 and the canal of Schlemm wall 90 without the need for making an incision by a separate cutting device before insertion of the intraocular stent 20. In aspects of the disclosure, the piercing member 40 may have any of a pointed tip, a blunted tip, a rounded tip, or any other suitable shape.

The first retention member 50 may have a chamfered sidewall 52 that provides for a sloped surface 54, where the tissue of the trabecular meshwork 94 and the canal of Schlemm wall 90 surrounding an opening created by the piercing member 40 may slide up and over the sloped surface 54 as the ocular stent 20 is inserted into position. A flange surface 56 is disposed at the widest portion of the chamfered sidewall 52, where the flange surface 56 may be configured to engage or be retained by the tissue of the canal of Schlemm wall 90 after the tissue of the canal of Schlemm wall 90 has contracted around the opening once the tissue has cleared the chamfered sidewall 52.

In aspects of the disclosure, the second retention member 60 may have a curved sidewall 62 having a narrow portion 64 (e.g., central portion) and a wide portion 66 (e.g., end portion). Similarly to the first retention member 50, the second retention member 60 is configured so that as the housing 30 slides through the opening in the trabecular meshwork 94, the tissue of the trabecular meshwork 94 slides up and over a housing mid-portion 32 and settles around the narrow portion 64 of the second retention member 60. The wide portion 66 of the second retention member 60 is configured to keep the tissue of the trabecular meshwork 94 located around the narrow portion 64, between the housing mid-portion 32 and the wide portion 66.

Once in place, the intraocular stent 20 is positioned so that an inlet port 72 of the central lumen 70 is disposed within an anterior chamber 96 of the eye and outlet ports 82 of the drainage tubes 80 are disposed within the canal of Schlemm 92. In use, aqueous humor in the anterior chamber 96 flows into and through the central lumen 70 and out through the drainage tubes 80/outlet ports 82 into the canal of Schlemm 92 (see FIG. 53).

Figure 4:
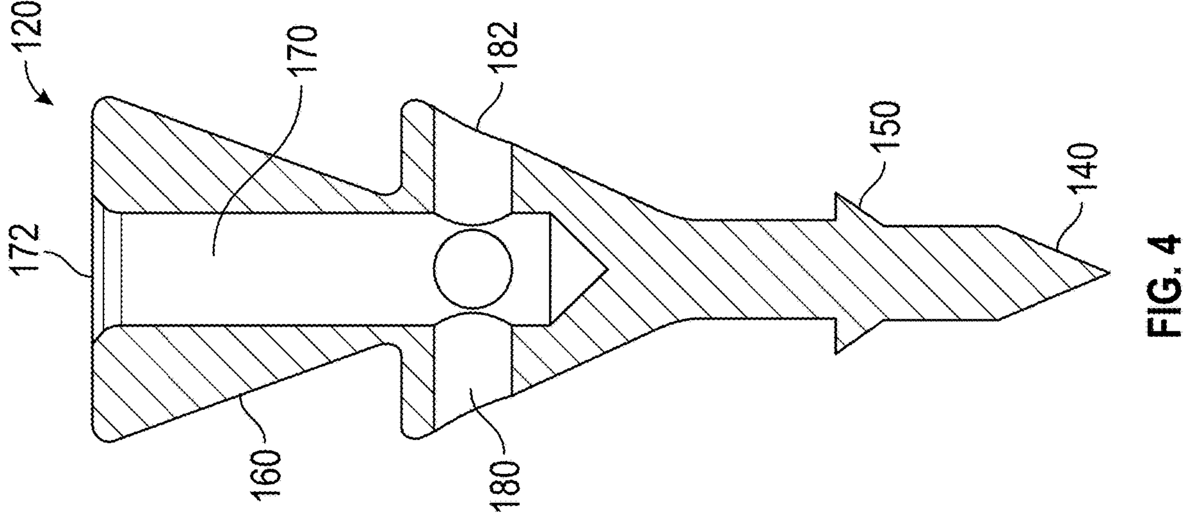
FIG. 4 depicts a cross-sectional front view of the intraocular stent of FIG. 3, according to aspects of the disclosure.
Figure 3:
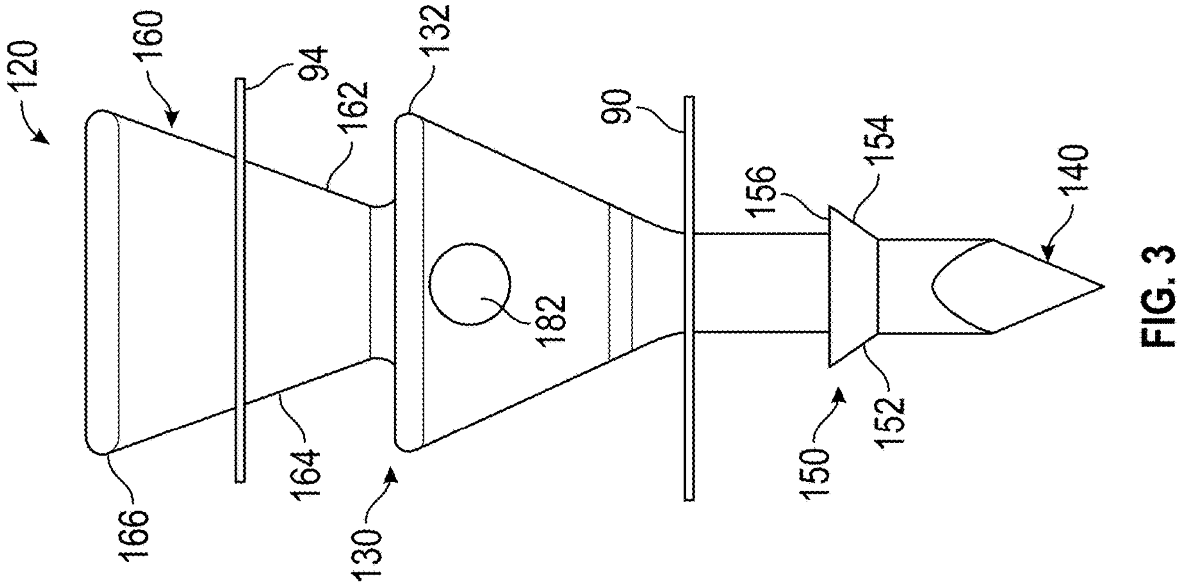
FIG. 3 depicts a front view of an intraocular stent, according to aspects of the disclosure.

As shown in FIGS. 3 and 4, an intraocular stent 120 may have a housing 130, a piercing member 140 extending from the housing 130, a first retention member 150 disposed on the piercing member 140, a second retention member 160 disposed on the housing 130, a central lumen 170 axially disposed within the housing 130 and multiple drainage tubes 180 coupled with the central lumen 170 and disposed within the housing 130. As further shown in FIG. 1, the intraocular stent 120 is positioned relative to the canal wall 90 of the canal of Schlemm 92 and the trabecular meshwork 94.

According to aspects of the disclosure, as shown in FIGS. 3 and 4, the piercing member 140 and the first retention member 150 may be configured the same as or similarly to the piercing member 40 and first retention member 50 of intraocular stent 20. In particular, the piercing member 140 may be a pointed spike configured to penetrate both the trabecular meshwork 94 and the canal of Schlemm wall 90 without the need for making an incision before insertion of the intraocular stent 120.

Also, the first retention member 150 may have a chamfered sidewall 152 that provides for a sloped surface 154, where the tissue of the trabecular meshwork 94 and the canal of Schlemm wall 90 surrounding an opening created by the piercing member 140 may slide up and over the sloped surface 154 as the ocular stent 120 is inserted into position. A flange surface 156 is disposed at the widest portion of the chamfered sidewall 152, where the flange surface 156 may be configured to engage or be retained by the tissue of the canal of Schlemm wall 90 after the tissue of the canal of Schlemm wall 90 has contracted around the opening once the tissue has cleared the chamfered sidewall 152.

In aspects of the disclosure, the second retention member 160 may have a chamfered sidewall 162 having a narrow portion 164 and a wide portion 166. Similarly to the first retention member 150, the second retention member 160 is configured so that as the housing 130 slides through the opening in the trabecular meshwork 94, the tissue of the trabecular meshwork 94 slides up and over a housing mid-portion 132 and settles around the narrow portion 164 of the second retention member 160. The wide portion 166 of the second retention member 160 is configured to keep the tissue of the trabecular meshwork 94 located around the narrow portion 164, between the housing mid-portion 132 and the wide portion 166.

Once in place, the intraocular stent 120 is positioned so that an inlet port 172 of the central lumen 170 is disposed within an anterior chamber 96 of the eye and outlet ports 182 of the drainage tubes 180 are disposed within the canal of Schlemm 92. In use, aqueous humor in the anterior chamber 96 flows into and through the central lumen 170 and out through the drainage tubes 180/outlet ports 182 into the canal of Schlemm 92.

Figure 6:
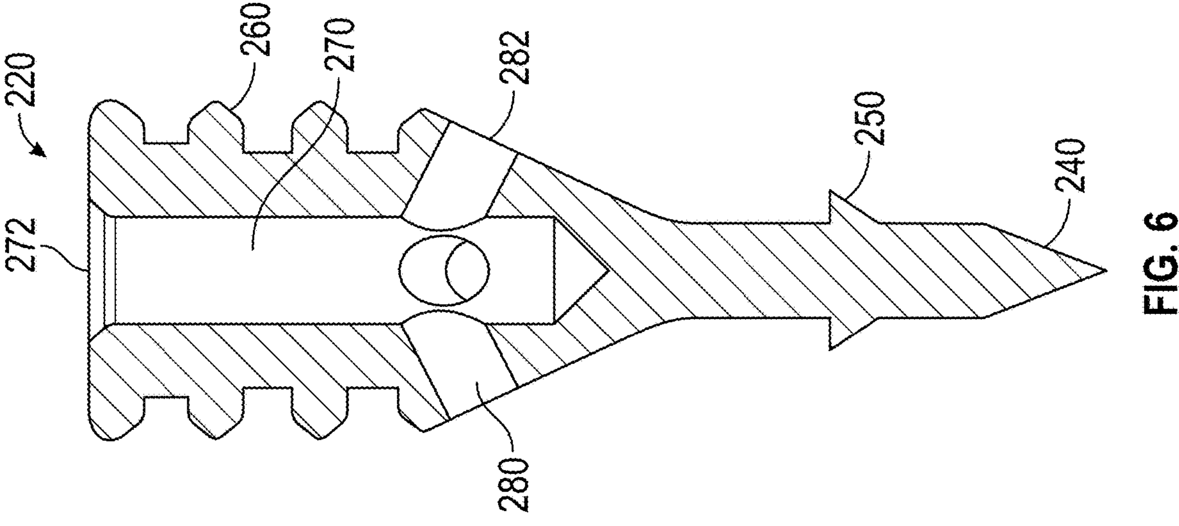
FIG. 6 depicts a cross-sectional front view of the intraocular stent of FIG. 5, according to aspects of the disclosure.
Figure 5:
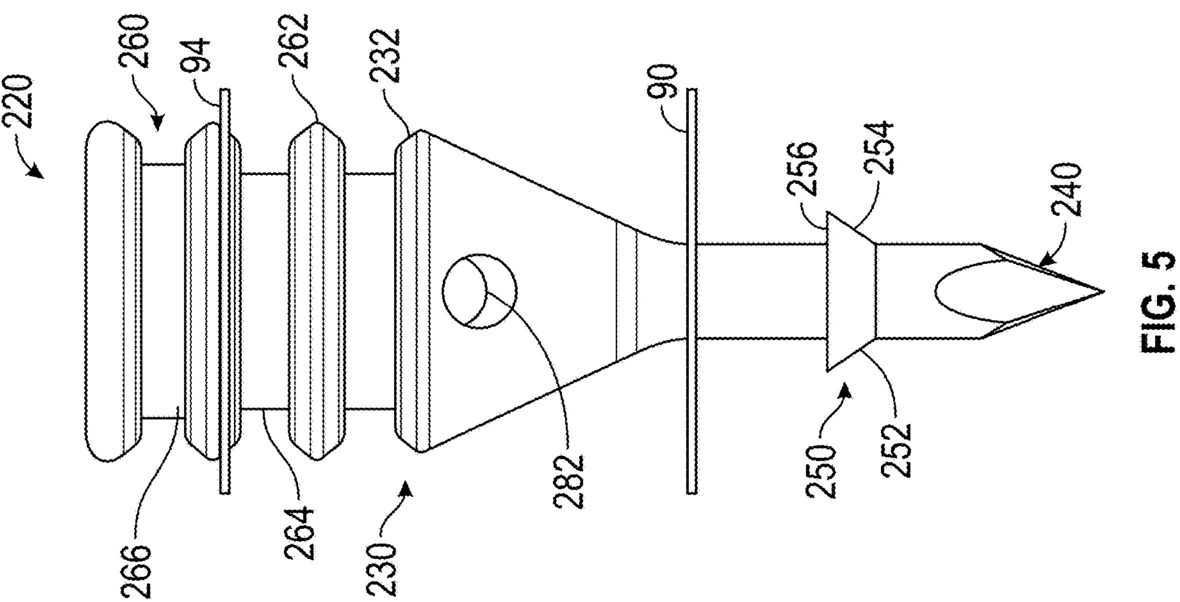
FIG. 5 depicts a front view of an intraocular stent, according to aspects of the disclosure.

As shown in FIGS. 5 and 6, an intraocular stent 220 may have a housing 230, a piercing member 240 extending from the housing 230, a first retention member 250 disposed on the piercing member 240, a second retention member 260 disposed on the housing 230, a central lumen 270 axially disposed within the housing 230 and multiple drainage tubes 280 coupled with the central lumen 270 and disposed within the housing 230. Here, the drainage tubes 280 are at a non-perpendicular angle to the central lumen 270 (e.g., 114 degrees), thus providing a less abrupt flow path change between the central lumen 270 and the drainage tubes 280. As further shown in FIG. 5, the intraocular stent 220 is positioned relative to the canal wall 90 of the canal of Schlemm 92 and the trabecular meshwork 94.

According to aspects of the disclosure, as shown in FIGS. 5 and 6, the piercing member 240 and the first retention member 250 may be configured the same as or similarly to the piercing member 40 and first retention member 50 of intraocular stent 20. In particular, the piercing member 240 may be a pointed spike configured to penetrate both the trabecular meshwork 94 and the canal of Schlemm wall 90 without the need for making an incision before insertion of the intraocular stent 220.

The first retention member 250 may have a chamfered sidewall 252 that provides for a sloped surface 254, where the tissue of the trabecular meshwork 94 and the canal of Schlemm wall 90 surrounding an opening created by the piercing member 240 may slide up and over the sloped surface 254 as the ocular stent 220 is inserted into position. A flange surface 256 is disposed at the widest portion of the chamfered sidewall 252, where the flange surface 256 may be configured to engage or be retained by the tissue of the canal of Schlemm wall 90 after the tissue of the canal of Schlemm wall 90 has contracted around the opening once the tissue has cleared the chamfered sidewall 252.

In aspects of the disclosure, the second retention member 260 may have multiple circular protrusions 262 disposed on a sidewall 264, with circular channels 266 disposed adjacent to the circular protrusions 262. The second retention member 260 is configured so that as the housing 230 slides through the opening in the trabecular meshwork 94, the tissue of the trabecular meshwork 94 slides up and over a housing mid-portion 232 and settles around one or more of the circular channels 266 and the circular protrusions 262 of the second retention member 260. The second retention member 260 is configured to keep the tissue of the trabecular meshwork 94 located between the housing mid-portion 232 and the endmost circular protrusion 262.

Once in place, the intraocular stent 220 is positioned so that an inlet port 272 of the central lumen 270 is disposed within an anterior chamber 96 of the eye and outlet ports 282 of the drainage tubes 280 are disposed within the canal of Schlemm 92. In use, aqueous humor in the anterior chamber 96 flows into and through the central lumen 270 and out through the drainage tubes 280/outlet ports 282 into the canal of Schlemm 92. Here, the fluid flow has a more gradual path change from the linear central lumen 270 to the angled drainage tubes 280.

As shown in FIGS. 7 to 10, an intraocular stent 320 may have a housing 330, a piercing member 340 extending from the housing 330, a first retention member 350 disposed on the piercing member 340, a second retention member 360 disposed on the housing 330, a central lumen 370 axially disposed within the housing 330 and multiple drainage tubes 380 disposed within the housing 330. Like the intraocular stent 20 shown in FIG. 1, the intraocular stent 320 may be inserted and similarly positioned relative to the canal wall 90 of the canal of Schlemm 92 and the trabecular meshwork 94.

Figure 8:
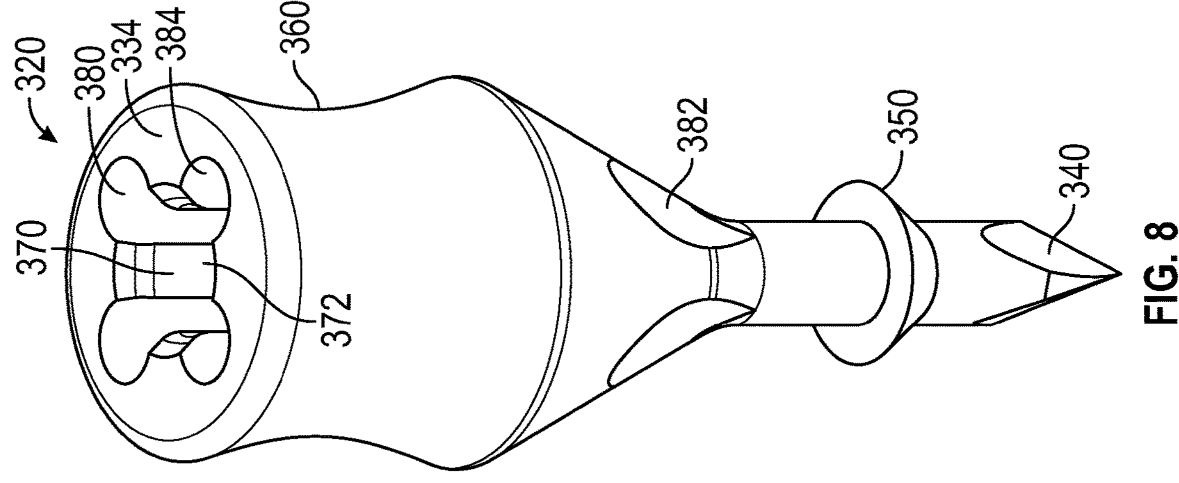
FIG. 8 depicts a perspective view of the intraocular stent of FIG. 7, according to aspects of the disclosure.
Figure 7:
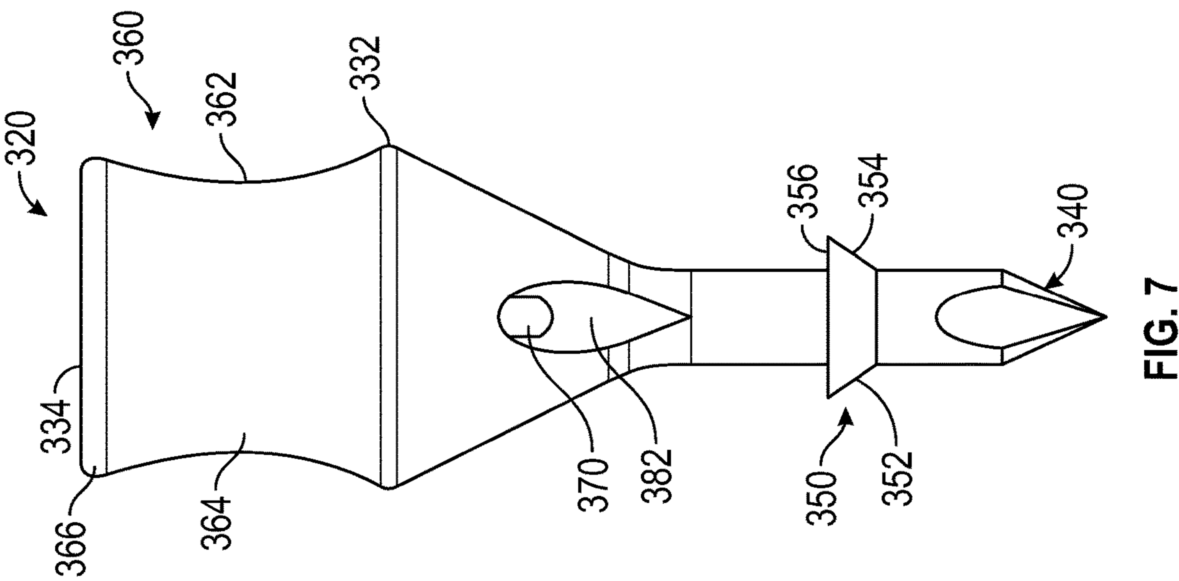
FIG. 7 depicts a front view of an intraocular stent with four parallel linear outlet ports, according to aspects of the disclosure.
Figure 10:
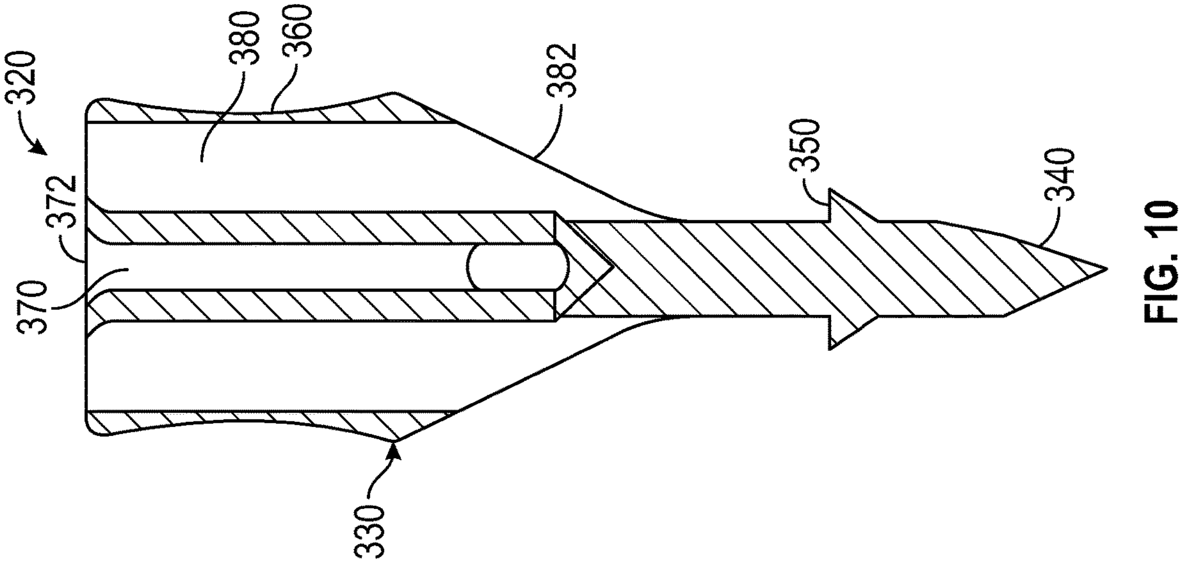
FIG. 10 depicts a cross-sectional front view of the intraocular stent of FIG. 7, according to aspects of the disclosure.
Figure 9:
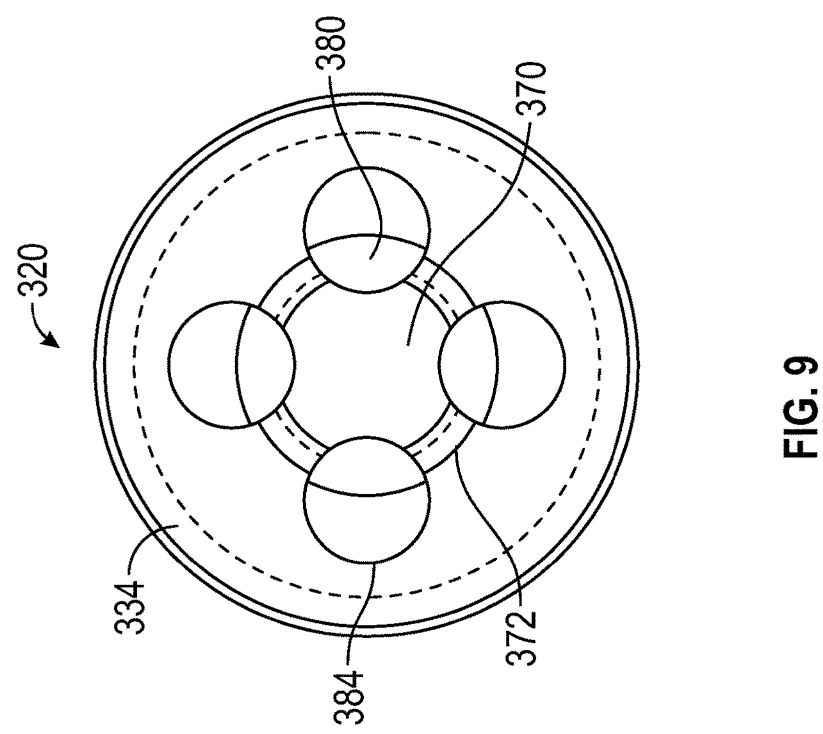
FIG. 9 depicts a top view of the intraocular stent of FIG. 7, according to aspects of the disclosure.

According to aspects of the disclosure, as shown in FIGS. 7 and 8, the piercing member 340 and the first retention member 350 may be configured the same as or similarly to the piercing member 40 and first retention member 50 of intraocular stent 20. In particular, the piercing member 340 may be a pointed spike configured to penetrate both the trabecular meshwork 94 and the canal of Schlemm wall 90 without the need for making an incision before insertion of the intraocular stent 320.

Also, the first retention member 350 may have a chamfered sidewall 352 that provides for a sloped surface 354, where the tissue of the trabecular meshwork 94 and the canal of Schlemm wall 90 surrounding an opening created by the piercing member 340 may slide up and over the sloped surface 354 as the intraocular stent 320 is inserted into position. A flange surface 356 is disposed at the widest portion of the chamfered sidewall 352, where the flange surface 356 may be configured to engage or be retained by the tissue of the canal of Schlemm wall 90 after the tissue of the canal of Schlemm wall 90 has contracted around the opening once the tissue has cleared the chamfered sidewall 352.

In aspects of the disclosure, the second retention member 360 may have a curved sidewall 362 having a narrow portion 364 and a wide portion 366. Similarly to the first retention member 350, the second retention member 360 is configured so that as the housing 330 slides through the opening in the trabecular meshwork 94, the tissue of the trabecular meshwork 94 slides up and over a housing mid-portion 332 and settles around the narrow portion 364 of the second retention member 360. The wide portion 366 of the second retention member 360 is configured to keep the tissue of the trabecular meshwork 94 located around the narrow portion 364, between the housing mid-portion 332 and the wide portion 366.

In aspects of the disclosure, the drainage tubes 380 are disposed through the housing 330 in parallel with the central lumen 370. Here, the central lumen 370 has an inlet port 372 disposed on a top surface 334 of the housing 330, while each drainage tube 380 has an outlet port 382 disposed below the housing mid-portion 332 and an inlet port 384 disposed on the top surface 334 of the housing 330. The drainage tubes 380 may be coupled to or intersect with the central lumen 370 such that the central lumen 370 and the drainage tubes 380 form a unified or single fluid pathway within the housing 330 for the length of the central lumen 370, as seen in FIG. 8.

Once in place, the intraocular stent 320 is positioned so that the inlet port 372 of the central lumen 370 and the inlet ports 384 of the drainage tubes 380 are disposed within an anterior chamber 96 of the eye and outlet ports 382 of the drainage tubes 380 are disposed within the canal of Schlemm 92. In use, aqueous humor in the anterior chamber 96 flows into and through the central lumen 370 and the drainage tubes 380, and out through the outlet ports 382 into the canal of Schlemm 92.

In aspects of the disclosure, the drainage tubes 380 may be angled relative to the axis of the housing 330. For example, the inlet ports 384 of the angled drainage tubes 380 may be disposed on the top surface 334 so that they are separate from the inlet port 372 of the central lumen 370. Here, portions of the drainage tubes 380 may intersect with or couple to the central lumen 370 within the housing 330 as the angle of each drainage tube 380 crosses the axial path of the central lumen 370.

In aspects of the disclosure, there may not be a central lumen and the drainage tubes 380 may be the sole fluid pathways for aqueous humor to flow through the intraocular stent 320. Here, the drainage tubes 380 may be disposed linearly along the axis of the housing 330 or angled with respect to the axis of the housing 330, for example.

In aspects of the disclosure, the drainage tubes 380 may each have a different diameter (e.g., smaller diameter) than the diameter of the central lumen 370. In aspects of the disclosure, the drainage tubes 380 may each have the same diameter as the diameter of the central lumen 370.

As shown in FIGS. 11 to 14, an intraocular stent 420 may have a housing 430, a piercing member 440 extending from the housing 430, a first retention member 450 disposed on the piercing member 440, a second retention member 460 disposed on the housing 430, a central lumen 470 axially disposed within the housing 430 and multiple drainage tubes 480 disposed within the housing 430. Like the intraocular stent 20 shown in FIG. 1, the intraocular stent 420 may be inserted and similarly positioned relative to the canal wall 90 of the canal of Schlemm 92 and the trabecular meshwork 94.

Figure 12:
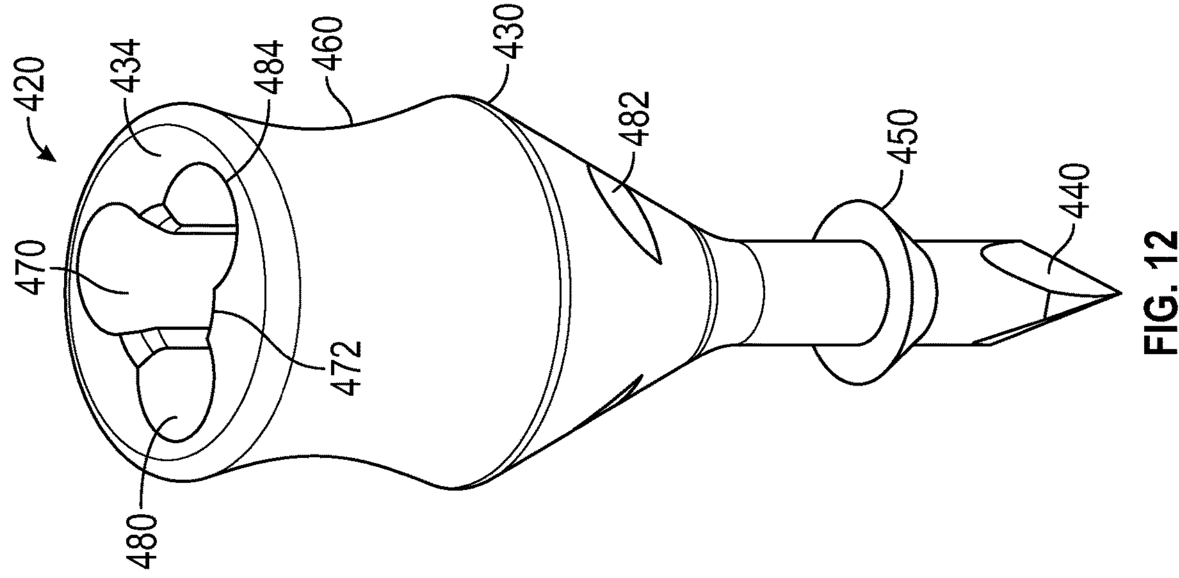
FIG. 12 depicts a perspective view of the intraocular stent of FIG. 11, according to aspects of the disclosure.
Figure 11:
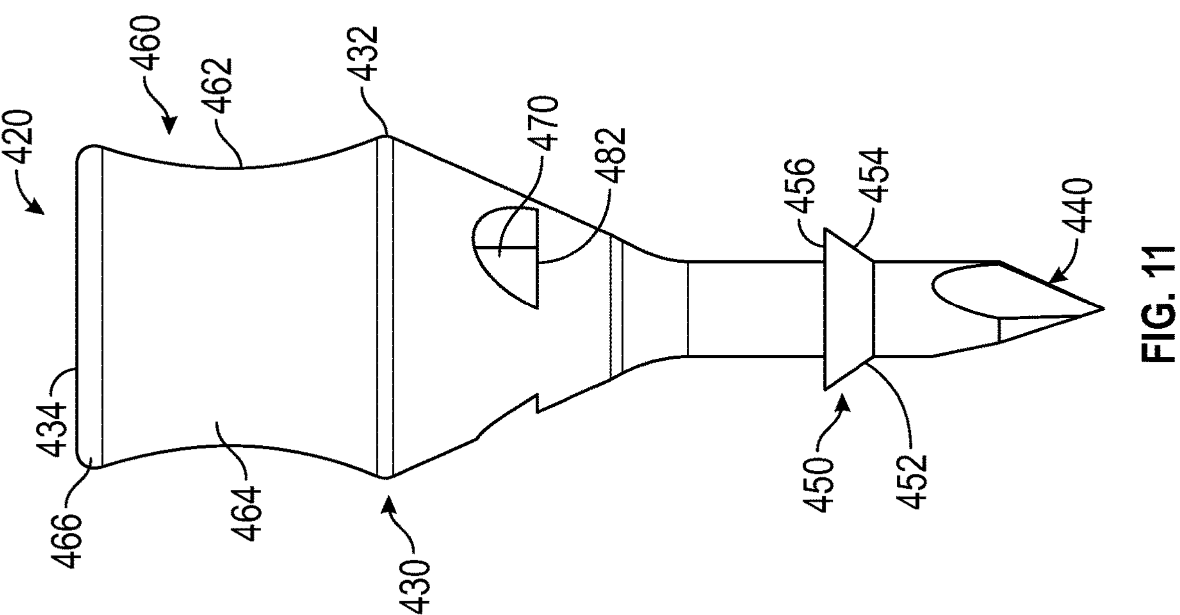
FIG. 11 depicts a front view of an intraocular stent with three parallel linear outlet ports, according to aspects of the disclosure.
Figure 14:
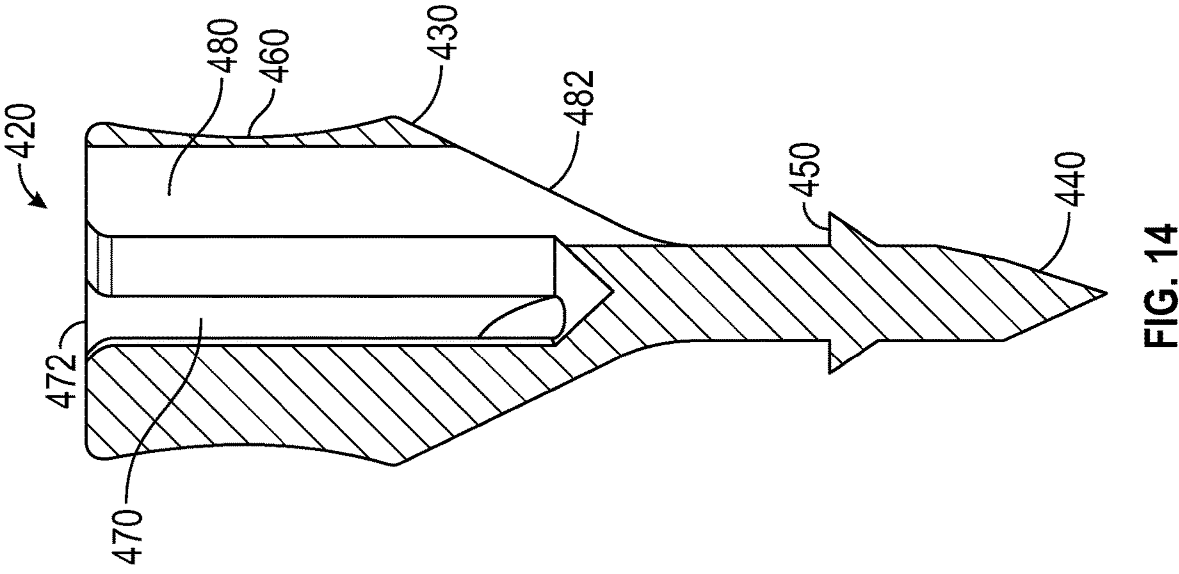
FIG. 14 depicts a cross-sectional front view of the intraocular stent of FIG. 11, according to aspects of the disclosure.
Figure 13:
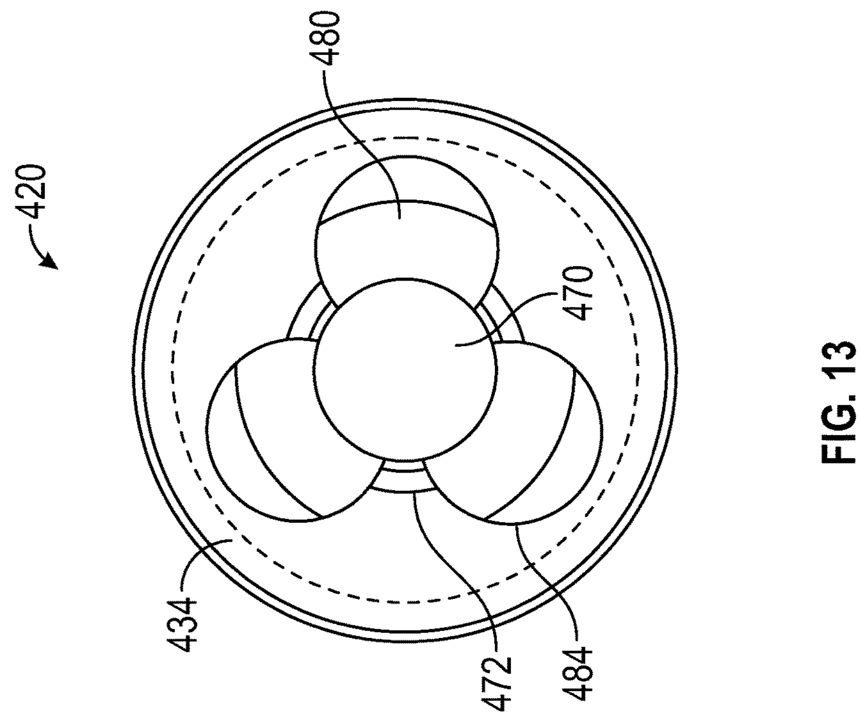
FIG. 13 depicts a top view of the intraocular stent of FIG. 11, according to aspects of the disclosure.

According to aspects of the disclosure, as shown in FIGS. 11 and 12, the piercing member 440 and the first retention member 450 may be configured the same as or similarly to the piercing member 40 and first retention member 50 of intraocular stent 20. In particular, the piercing member 440 may be a pointed spike configured to penetrate both the trabecular meshwork 94 and the canal of Schlemm wall 90 without the need for making an incision before insertion of the intraocular stent 420.

Also, the first retention member 450 may have a chamfered sidewall 452 that provides for a sloped surface 454, where the tissue of the trabecular meshwork 94 and the canal of Schlemm wall 90 surrounding an opening created by the piercing member 440 may slide up and over the sloped surface 454 as the intraocular stent 420 is inserted into position. A flange surface 456 is disposed at the widest portion of the chamfered sidewall 452, where the flange surface 456 may be configured to engage or be retained by the tissue of the canal of Schlemm wall 90 after the tissue of the canal of Schlemm wall 90 has contracted around the opening once the tissue has cleared the chamfered sidewall 452.

In aspects of the disclosure, the second retention member 460 may have a curved sidewall 462 having a narrow portion 464 and a wide portion 466. Similarly to the first retention member 450, the second retention member 460 is configured so that as the housing 430 slides through the opening in the trabecular meshwork 94, the tissue of the trabecular meshwork 94 slides up and over a housing mid-portion 432 and settles around the narrow portion 464 of the second retention member 460. The wide portion 466 of the second retention member 460 is configured to keep the tissue of the trabecular meshwork 94 located around the narrow portion 464, between the housing mid-portion 432 and the wide portion 466.

In aspects of the disclosure, the drainage tubes 480 are disposed through the housing 430 in parallel with the central lumen 470. Here, the central lumen 470 has an inlet port 472 disposed on a top surface 434 of the housing 430, while each drainage tube 480 has an outlet port 482 disposed below the housing mid-portion 432 and an inlet port 484 disposed on the top surface 434 of the housing 430. The drainage tubes 480 may be coupled to or intersect with the central lumen 470 such that the central lumen 470 and the drainage tubes 480 form a unified or single fluid pathway within the housing 430 for the length of the central lumen 470, as seen in FIG. 12.

Once in place, the intraocular stent 420 is positioned so that the inlet port 472 of the central lumen 470 and the inlet ports 484 of the drainage tubes 480 are disposed within an anterior chamber 96 of the eye and outlet ports 482 of the drainage tubes 480 are disposed within the canal of Schlemm 92. In use, aqueous humor in the anterior chamber 96 flows into and through the central lumen 470 and the drainage tubes 480, and out through the outlet ports 482 into the canal of Schlemm 92.

In aspects of the disclosure, the drainage tubes 480 may be angled relative to the linear axis of the housing 430. For example, the inlet ports 484 of the angled drainage tubes 480 may be disposed on the top surface 434 so that they are separate from the inlet port 472 of the central lumen 470. Here, portions of the drainage tubes 480 may intersect with or couple to the central lumen 470 within the housing 430 as the angle of each drainage tube 480 crosses the axial path of the central lumen 470.

In aspects of the disclosure, there may not be a central lumen and the drainage tubes 480 may be the sole fluid pathways for aqueous humor to flow through the intraocular stent 420. Here, the drainage tubes 480 may be disposed linearly along the axis of the housing 430 or angled with respect to the axis of the housing 430, for example.

In aspects of the disclosure, the drainage tubes 480 may each have a different diameter (e.g., smaller diameter) than the diameter of the central lumen 470. In aspects of the disclosure, the drainage tubes 480 may each have the same diameter as the diameter of the central lumen 470.

Figure 16:
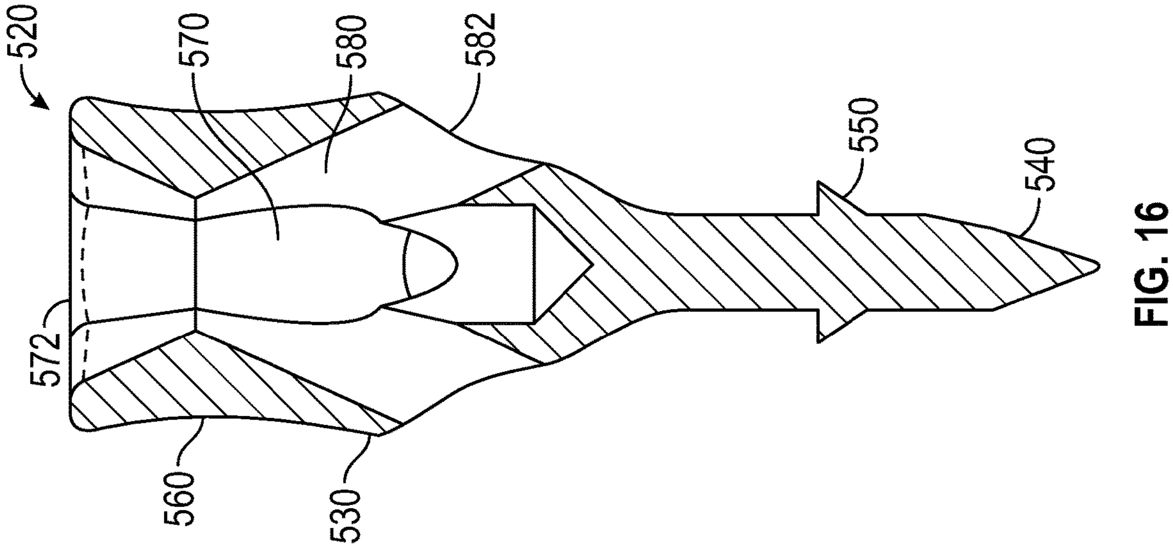
FIG. 16 depicts a cross-sectional front view of the intraocular stent of FIG. 15, according to aspects of the disclosure.
Figure 15:
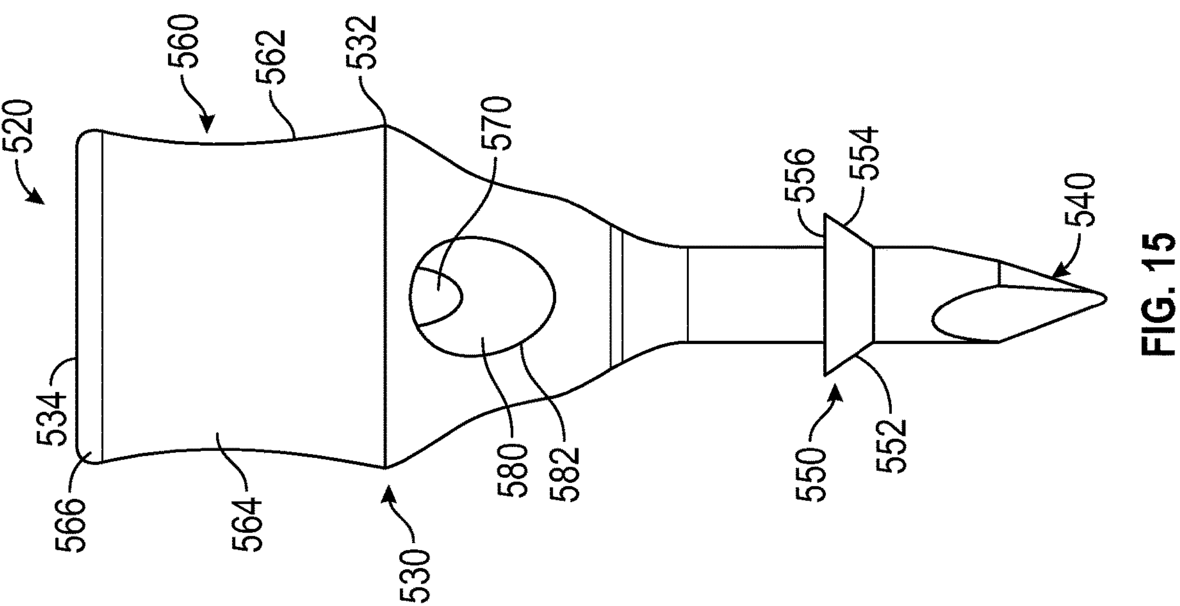
FIG. 15 depicts a front view of an intraocular stent with four angled linear outlet ports, according to aspects of the disclosure.

As shown in FIGS. 15 and 16, an intraocular stent 520 may have a housing 530, a piercing member 540 extending from the housing 530, a first retention member 550 disposed on the piercing member 540, a second retention member 560 disposed on the housing 530, a central lumen 570 axially disposed within the housing 330 and multiple drainage tubes 580 disposed within the housing 530. Like the intraocular stent 20 shown in FIG. 1, the intraocular stent 520 may be inserted and similarly positioned relative to the canal wall 90 of the canal of Schlemm 92 and the trabecular meshwork 94.

According to aspects of the disclosure, as shown in FIGS. 15 and 16, the piercing member 540 and the first retention member 550 may be configured the same as or similarly to the piercing member 40 and first retention member 50 of intraocular stent 20. In particular, the piercing member 540 may be a pointed spike configured to penetrate both the trabecular meshwork 94 and the canal of Schlemm wall 90 without the need for making an incision before insertion of the intraocular stent 520.

Also, the first retention member 550 may have a chamfered sidewall 552 that provides for a sloped surface 554, where the tissue of the trabecular meshwork 94 and the canal of Schlemm wall 90 surrounding an opening created by the piercing member 540 may slide up and over the sloped surface 554 as the intraocular stent 520 is inserted into position. A flange surface 556 is disposed at the widest portion of the chamfered sidewall 552, where the flange surface 556 may be configured to engage or be retained by the tissue of the canal of Schlemm wall 90 after the tissue of the canal of Schlemm wall 90 has contracted around the opening once the tissue has cleared the chamfered sidewall 552.

In aspects of the disclosure, the second retention member 560 may have a curved sidewall 562 having a narrow portion 564 and a wide portion 566. Similarly to the first retention member 550, the second retention member 560 is configured so that as the housing 530 slides through the opening in the trabecular meshwork 94, the tissue of the trabecular meshwork 94 slides up and over a housing mid-portion 532 and settles around the narrow portion 564 of the second retention member 560. The wide portion 566 of the second retention member 560 is configured to keep the tissue of the trabecular meshwork 94 located around the narrow portion 564, between the housing mid-portion 532 and the wide portion 566.

In aspects of the disclosure, the drainage tubes 580 are disposed through the housing 530 at an angle to the central lumen 570. Here, the central lumen 570 has an inlet port 572 disposed on a top surface 534 of the housing 530, while each drainage tube 580 has an outlet port 582 disposed below the housing mid-portion 532 and an inlet port 584 disposed on the top surface 534 of the housing 530. Each drainage tube 580 may be linear from the top surface 534 to the outlet port 582, thus facilitating free fluid flow through the drainage tube 580 and preventing or minimizing clogging by particles from the eye. Each drainage tube 580 may be coupled to or intersect with a portion of the central lumen 570.

Once in place, the intraocular stent 520 is positioned so that the inlet port 572 of the central lumen 570 and the inlet ports 584 of the drainage tubes 580 are disposed within an anterior chamber 96 of the eye and outlet ports 582 of the drainage tubes 580 are disposed within the canal of Schlemm 92. In use, aqueous humor in the anterior chamber 96 flows into and through the central lumen 570 and the drainage tubes 580, and out through the outlet ports 582 into the canal of Schlemm 92.

In aspects of the disclosure, there may not be a central lumen and the drainage tubes 580 may be the sole fluid pathways for aqueous humor to flow through the intraocular stent 520.

In aspects of the disclosure, the drainage tubes 580 may each have a different diameter (e.g., smaller diameter) than the diameter of the central lumen 570. In aspects of the disclosure, the drainage tubes 580 may each have the same diameter as the diameter of the central lumen 570.

Figure 17:
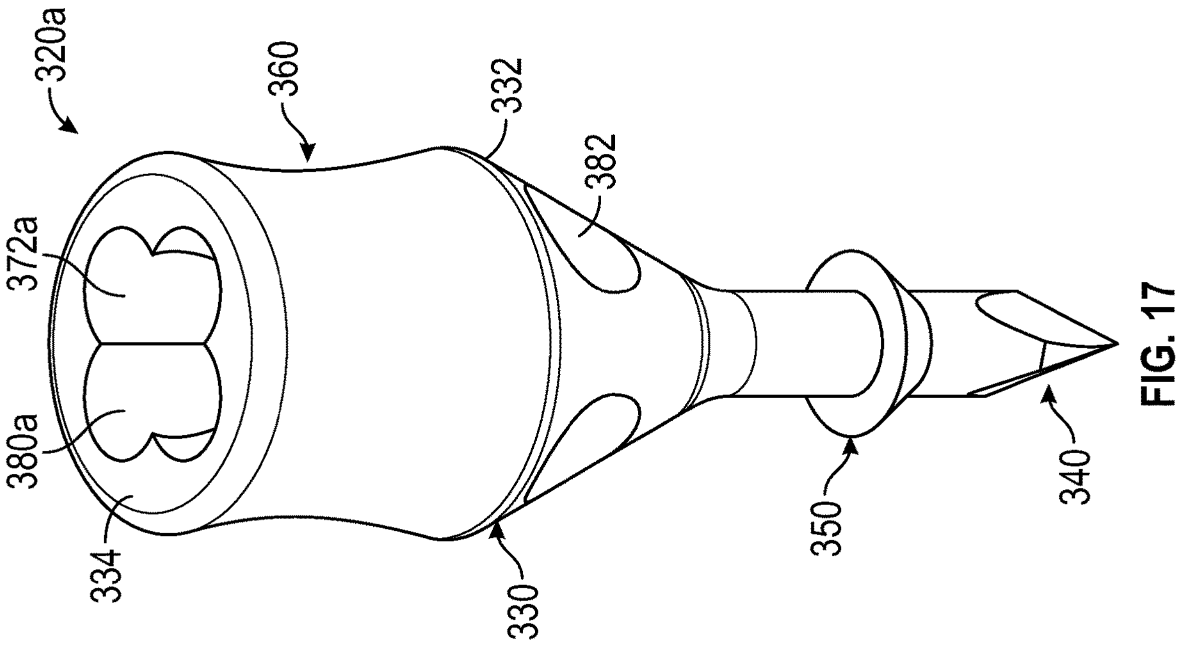
FIG. 17 depicts a perspective view of an intraocular stent with four merged parallel linear outlet ports, according to aspects of the disclosure.

As shown in FIG. 17, an intraocular stent **320*a* may be similar to intraocular stent 320 by having the housing 330, the piercing member 340 extending from the housing 330, the first retention member 350 disposed on the piercing member 340, and the second retention member 360 disposed on the housing 330 as provided in intraocular stent 320. The intraocular stent 320*a* differs from intraocular stent 320 in that there is no separate central lumen 370 axially disposed within the housing 330 while multiple drainage tubes 380*a* are merged together within the housing 330. Thus, the merged drainage tubes 380*a* form a single inlet port 372*a* disposed on the top surface 334 of the housing 330, while each drainage tube 380*a* has an outlet port 382 disposed below the housing mid-portion 332**.

Figure 18:
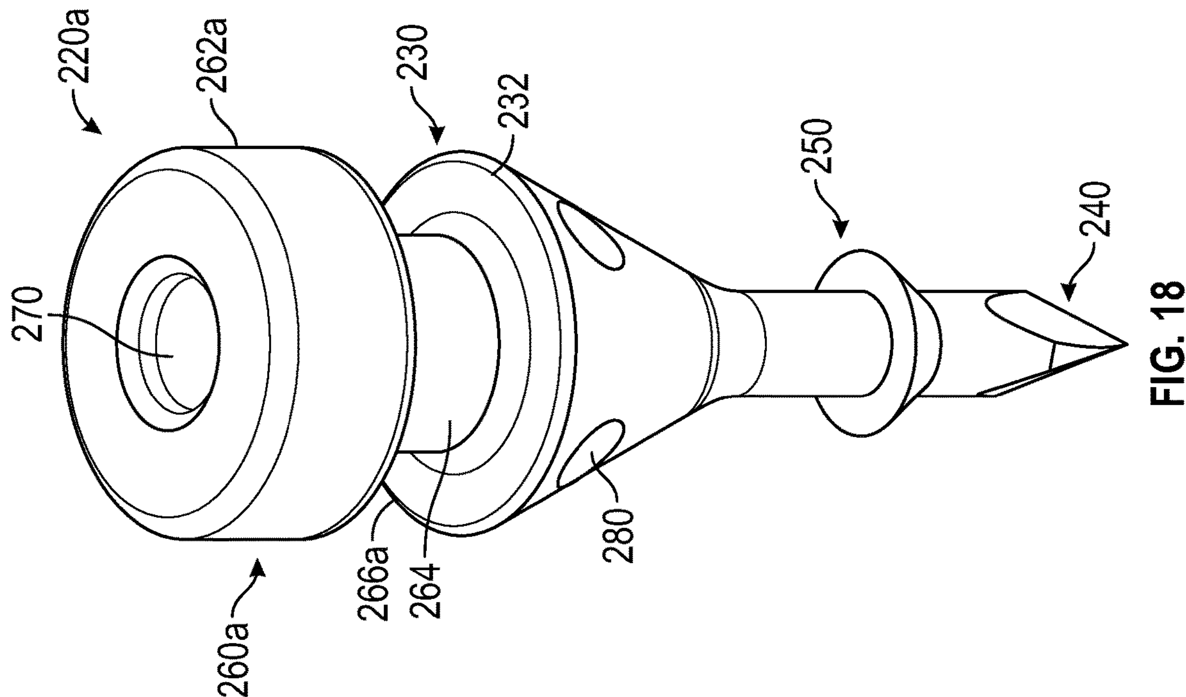
FIG. 18 depicts a perspective view of an intraocular stent, according to aspects of the disclosure.

As shown in FIG. 18, an intraocular stent **220*a* may be similar to intraocular stent 220, having the housing 230, the piercing member 240 extending from the housing 230, the first retention member 250 disposed on the piercing member 240, a central lumen 270 axially disposed within the housing 230 and multiple drainage tubes 280 coupled with the central lumen 270 and disposed within the housing 230. The intraocular stent 220*a* differs from intraocular stent 220 in that a second retention member 260*a* disposed on the housing 230 is shaped differently than the second retention member 260. Here, the second retention member 260*a* has one circular protrusion 262*a* disposed on the sidewall 264, with one circular channel 266*a* disposed between the circular protrusion 262*a* and the housing mid-portion 232**.

Figure 20:
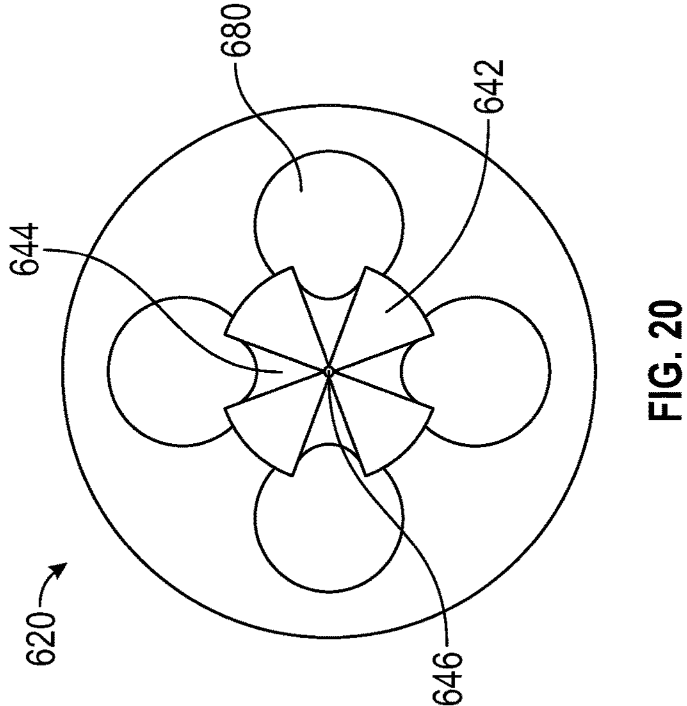
FIG. 20 depicts a bottom view of the intraocular stent of FIG. 19, according to aspects of the disclosure.
Figure 19:
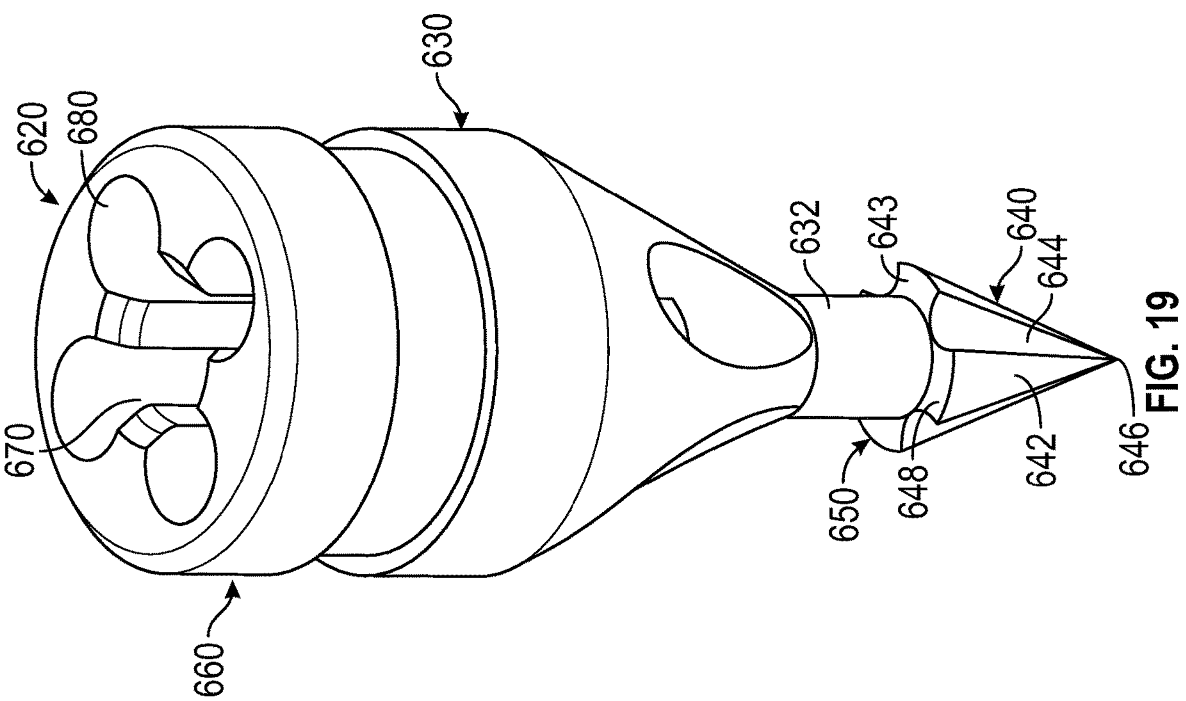
FIG. 19 depicts a perspective view of an intraocular stent, according to aspects of the disclosure.

As shown in FIGS. 19 and 20, an intraocular stent 620 may have a housing 630, a piercing member 640 extending from a cylindrical bottom portion 632 of the housing 630, a first retention member 650 disposed on the piercing member 640, a second retention member 660 disposed on the housing 630, a central lumen 670 axially disposed within the housing 630 and multiple drainage tubes 680 disposed within the housing 630. Like the above-described intraocular stents 20, 120, 220, **220*a*, 320, 320*a*, 420, 520, the intraocular stent 620 may be inserted and similarly positioned relative to the canal wall 90 of the canal of Schlemm 92 and the trabecular meshwork 94**.

The piercing member 640 may be a pointed spike configured to penetrate both the trabecular meshwork 94 and the canal of Schlemm wall 90 without the need for making an incision before insertion of the intraocular stent 620. The piercing member 640 may have a cross-shaped configuration with multiple protrusions 642 and multiple shaped grooves 644 interspersed between the protrusions 642. The protrusions 642 may taper outward between a leading end 646 (e.g., pointed tip) and a flared end 648, where the flared end 648 terminates at the cylindrical bottom portion 632. Upper surfaces 643 of the protrusions 642 define and/or form the first retention member 650.

Figure 22:
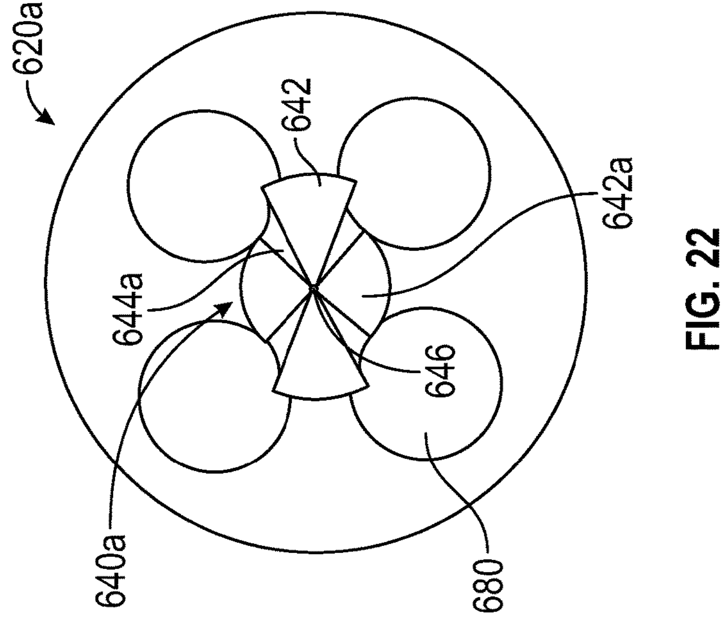
FIG. 22 depicts a bottom view of the intraocular stent of FIG. 21, according to aspects of the disclosure.
Figure 21:
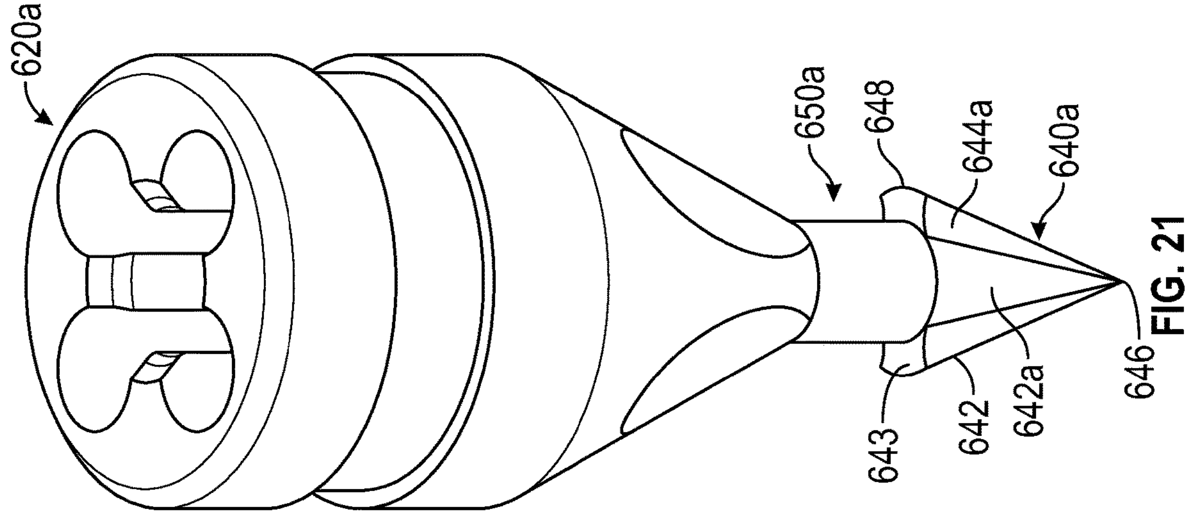
FIG. 21 depicts a perspective view of an intraocular stent, according to aspects of the disclosure.

As shown in FIGS. 21 and 22, the intraocular stent **620*a* may differ from intraocular stent 620 only in the piercing member 640*a* and the retention member 650*a*. Here, two opposing protrusions 642 are the same, while two other protrusions 642*a* are much shallower, such that the outward tapering of the protrusions 642 is much more pronounced than the outward tapering of the protrusions 642*a*. Thus, grooves 644*a* have a different configuration (e.g., shape, taper, depth) than grooves 644 of intraocular stent 620. The upper surfaces 643 of the two protrusions 642 define and/or form the first retention member 650*a***.

Figures 23, 24, 25:
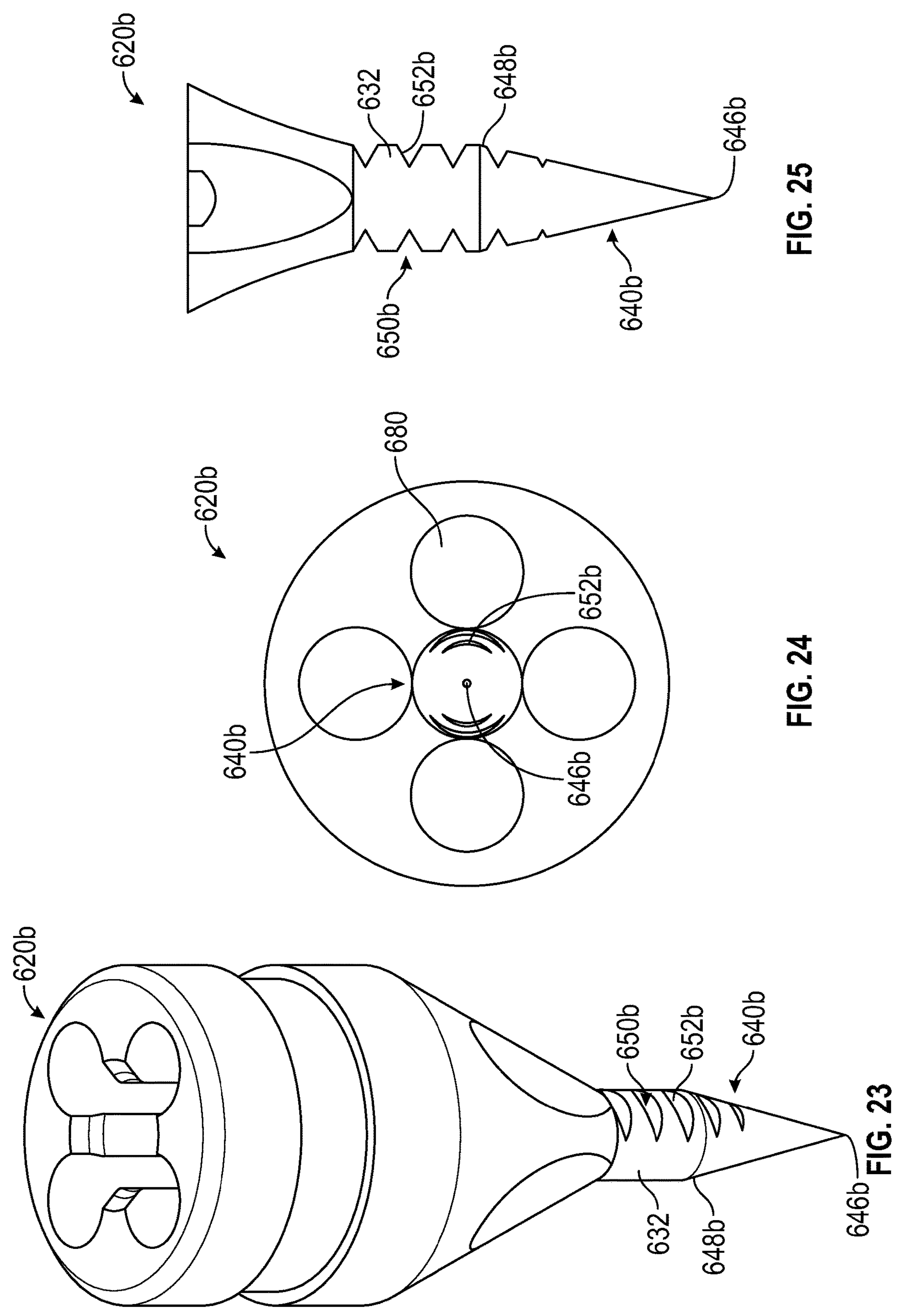
FIG. 23 depicts a perspective view of an intraocular stent, according to aspects of the disclosure.
FIG. 24 depicts a bottom view of the intraocular stent of FIG. 23, according to aspects of the disclosure.
FIG. 25 depicts a partial front view of the intraocular stent of FIG. 23, according to aspects of the disclosure.

As shown in FIGS. 23 to 25, the intraocular stent **620*b* may differ from intraocular stent 620 only in the piercing member 640*b* and the retention member 650*b*. Here, the piercing member 640*b* is configured as a conical portion that tapers outward between a leading end 646*b* (e.g., pointed tip) and a flared end 648*b* that terminates at the cylindrical bottom portion 632. The first retention member 650*b* is defined and/or formed from multiple notches 652*b* disposed in both the piercing member 640*b* and the cylindrical bottom portion 632**.

As shown in FIG. 25, the notches **652*b* may be configured as opposing pairs. Thus, each pair of opposing notches 652*b* may be configured to engage or be retained by the tissue of the canal of Schlemm wall 90 after the tissue of the canal of Schlemm wall 90 has contracted around the opening. Accordingly, piercing member 640*b* and first retention member 650*b* may provide multiple levels for retention, thus providing for adjustability of the intraocular stent 620*b* relative to the canal of Schlemm wall 90**.

In aspects of the disclosure, the notches **652*b* may be disposed on only one of the piercing member 640*b* and the cylindrical bottom portion 632. In aspects of the disclosure, the notches 652*b* may be disposed on only one side of the piercing member 640*b* and/or the cylindrical bottom portion 632. In aspects of the disclosure, the notches 652*b* may extend around the entire circumference of the piercing member 640*b* and/or the cylindrical bottom portion 632**.

Figures 26, 27, 28:
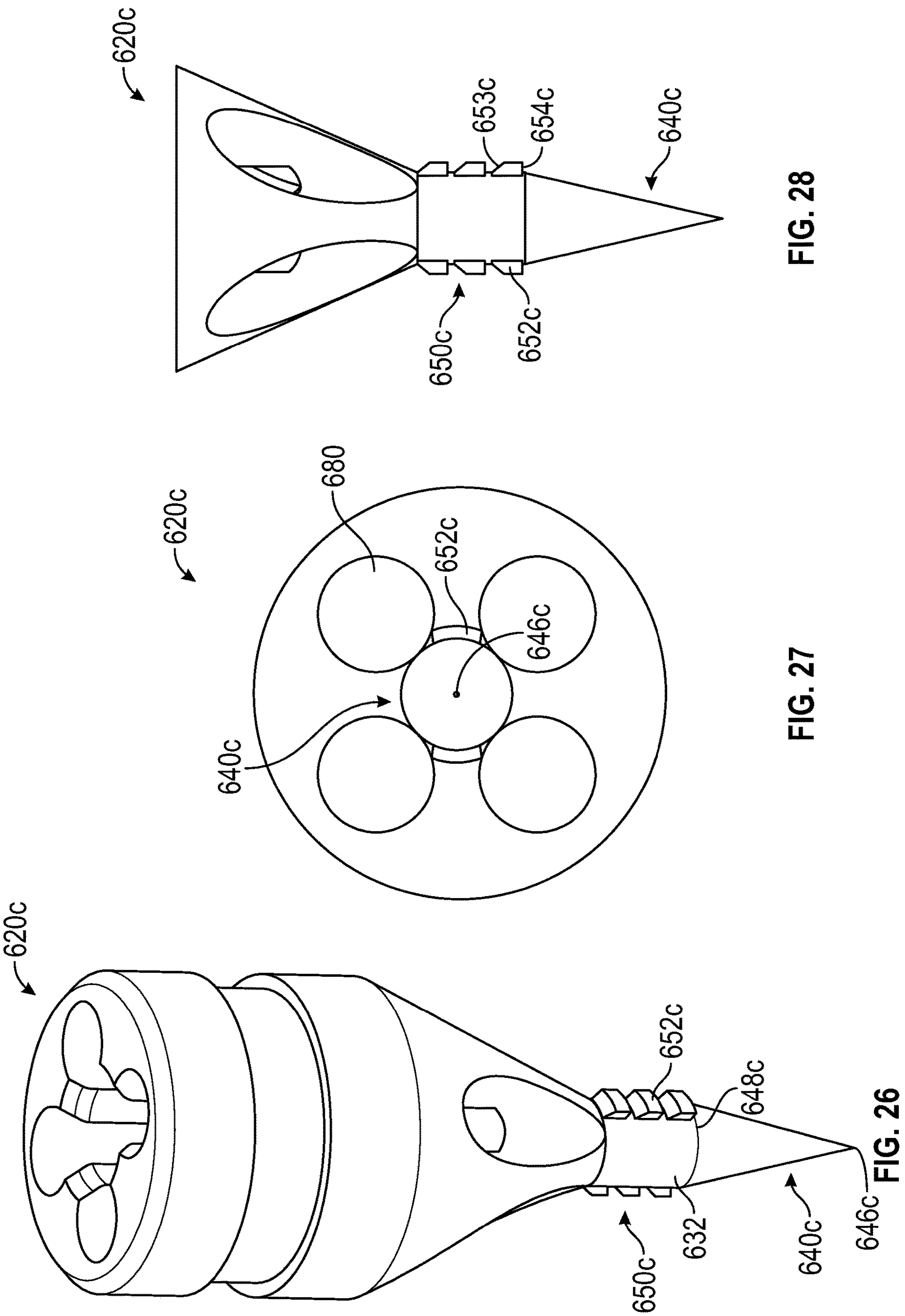
FIG. 26 depicts a perspective view of an intraocular stent, according to aspects of the disclosure.
FIG. 27 depicts a bottom view of the intraocular stent of FIG. 26, according to aspects of the disclosure.
FIG. 28 depicts a partial front view of the intraocular stent of FIG. 26, according to aspects of the disclosure.
Figures 29, 30, 31:
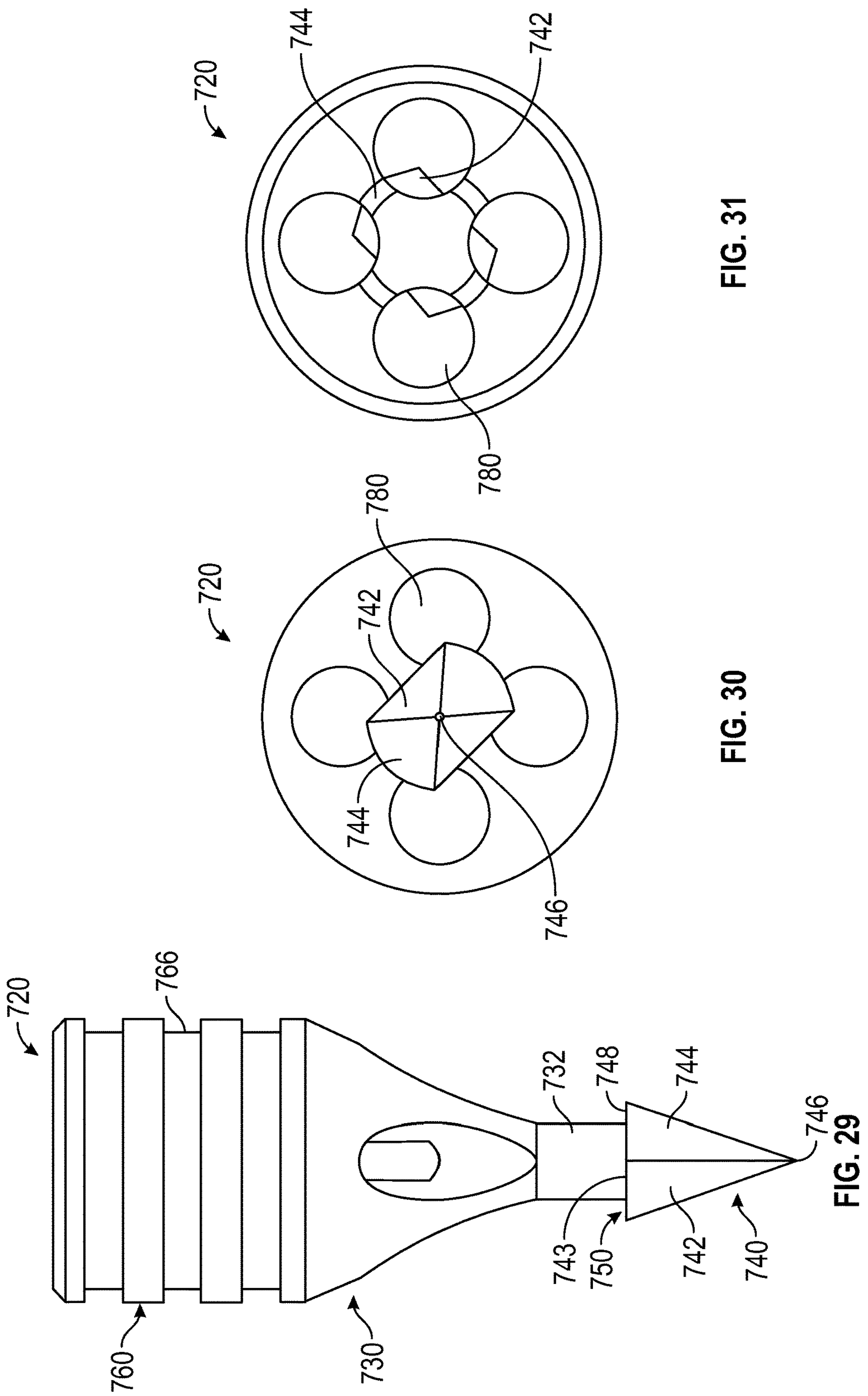
FIG. 29 depicts a front view of an intraocular stent, according to aspects of the disclosure.
FIG. 30 depicts a bottom view of the intraocular stent of FIG. 29, according to aspects of the disclosure.
FIG. 31 depicts a top view of the intraocular stent of FIG. 29, according to aspects of the disclosure.

As shown in FIGS. 26 to 28, the intraocular stent **620*c* may differ from intraocular stent 620 only in the piercing member 640*c* and the retention member 650*c*. Here, the piercing member 640*c* is configured as a conical portion that tapers outward between a leading end 646*c* (e.g., pointed tip) and a flared end 648*c* that terminates at the cylindrical bottom portion 632, similarly to piercing member 640*b*. The first retention member 650*c* is defined and/or formed from multiple projections 652*c* disposed on the cylindrical bottom portion 632. The projections 652*c* may have cambered (e.g., slanted, angled) trailing ends 653*c* and orthogonal (e.g., perpendicular) leading ends 654*c***.

As shown in FIG. 28, the projections **652*c* may be configured as opposing pairs. Thus, each pair of opposing projections 652*c* may be configured to engage or be retained by the tissue of the canal of Schlemm wall 90 after the tissue of the canal of Schlemm wall 90 has contracted around the opening. Accordingly, first retention member 650*c* may provide multiple levels for retention, thus providing for adjustability of the intraocular stent 620***c* relative to the canal of Schlemm wall 90.

In aspects of the disclosure, the projections 652*c* may be disposed on both of the piercing member 640*c* and the cylindrical bottom portion 632. In aspects of the disclosure, the projections 652*c* may be disposed on only one side of the piercing member 640*c* and/or the cylindrical bottom portion 632. In aspects of the disclosure, the projections 652*c* may extend around the entire circumference of the piercing member 640*c* and/or the cylindrical bottom portion 632.

In aspects of the disclosure, any of the above-described intraocular stents 20, 120, 220, 220*a*, 320, 320*a*, 420, 520 may have any of the above-described piercing member/first retention member combinations 640/650, 640*a*/650*a*, 640*b*/650*b*, 640*c*/650*c*.

As shown in FIGS. 29 to 33, an intraocular stent 720 may have a housing 730, a piercing member 740 extending from a cylindrical bottom portion 732 of the housing 730, a first retention member 750 disposed on the piercing member 740, a second retention member 760 disposed on the housing 730, and multiple drainage tubes 780 disposed within the housing 730. Like the above-described intraocular stents 20, 120, 220, 220*a*, 320, 320*a*, 420, 520, 620, 620*a*, 620*b*, 620*c*, the intraocular stent 720 may be inserted and similarly positioned relative to the canal wall 90 of the canal of Schlemm 92 and the trabecular meshwork 94.

Here, the second retention member 760 may be configured similarly to that of second retention member 260. In aspects of the disclosure, the multiple circular channels 766 provide a depth indication during installation of the intraocular stent 720.

Figure 33:
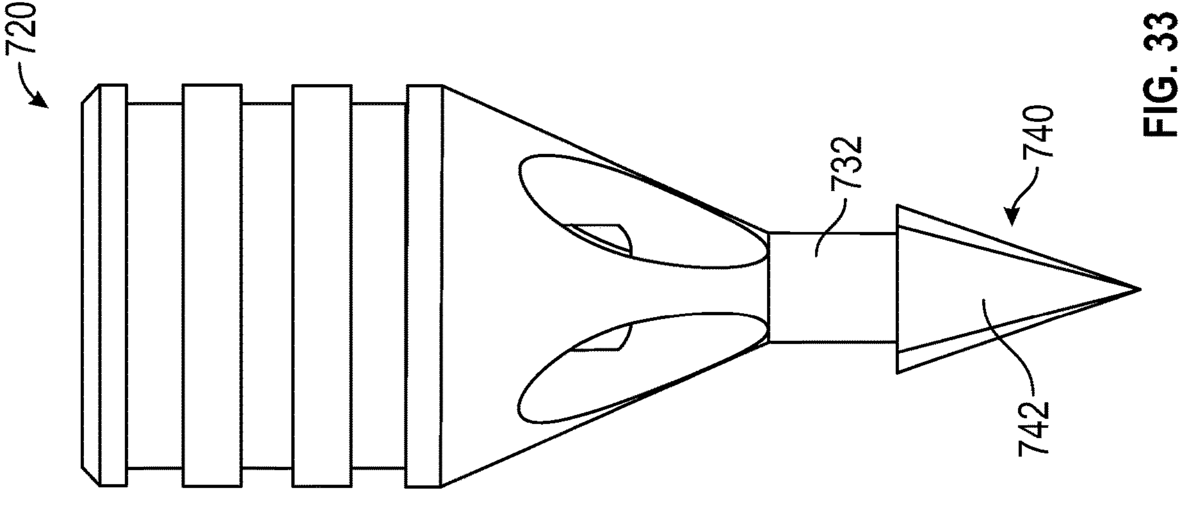
FIG. 33 depicts another angled front view of the intraocular stent of FIG. 29, according to aspects of the disclosure.
Figure 32:
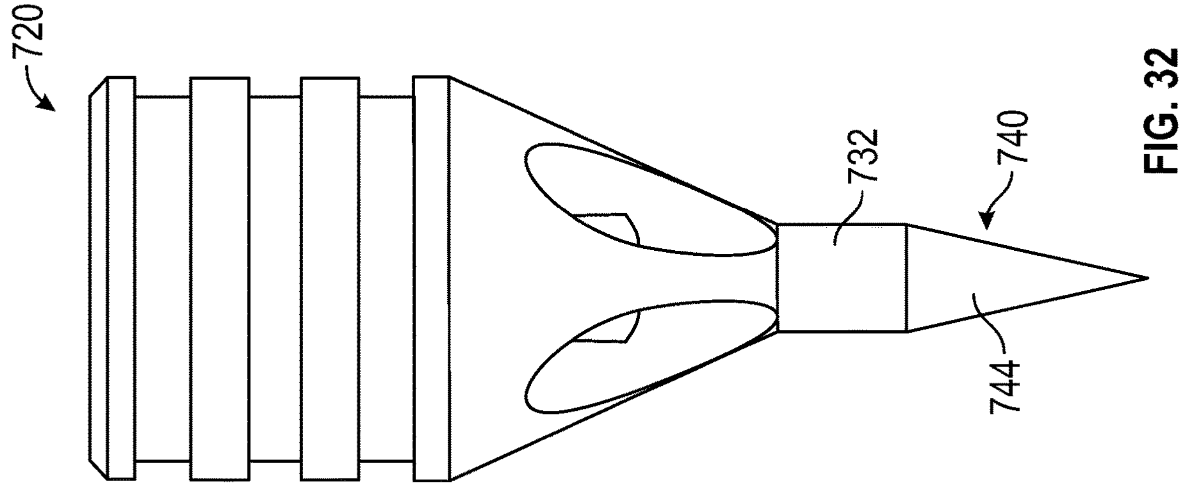
FIG. 32 depicts an angled front view of the intraocular stent of FIG. 29, according to aspects of the disclosure.

The piercing member 740 may be configured in a rectangular type shape having two opposing planar walls 742 and two opposing convex walls 744. The walls 742, 744 may taper outward between a leading end 746 (e.g., pointed tip) and a flared end 748, where the flared end 748 terminates at the cylindrical bottom portion 732. An upper surface 743 of the flared end 748 defines and/or forms the first retention member 750. The piercing member 740 may have a slim profile in one angled front view as shown in FIG. 32, where the flared end 748 and the cylindrical bottom portion 732 have the same width, and have a wide profile in another angled front view (e.g., rotated 90 degrees) as shown in FIG. 33, where the flared end 748 is wider than the width of the cylindrical bottom portion 732. In aspects of the disclosure, the alternating slim and wide profiles of the piercing member 740 (e.g., harpoon) provide for easy penetration into the tissue and good anchoring in the tissue.

Figure 34:
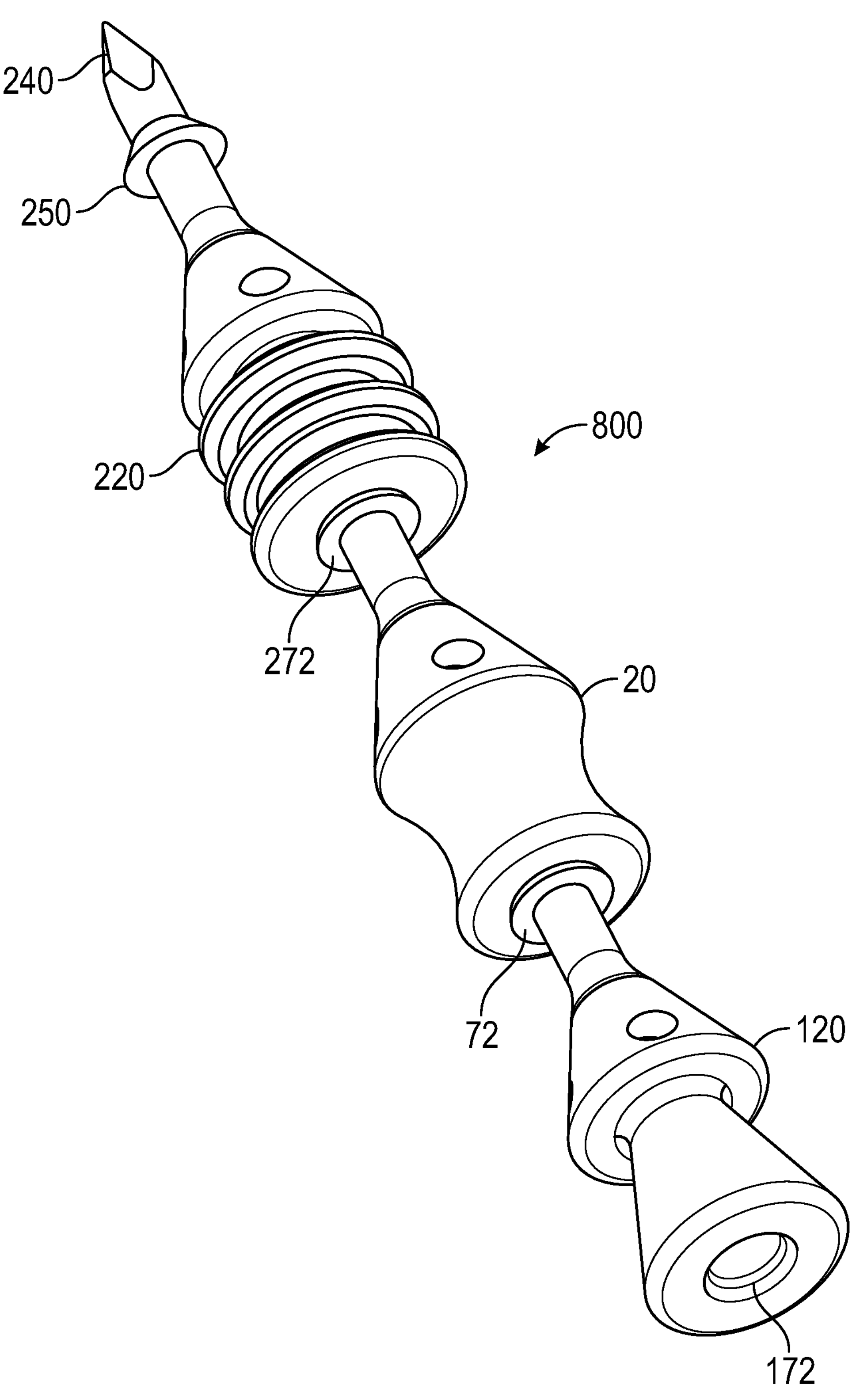
FIG. 34 depicts a perspective view of an intraocular stent stack, according to aspects of the disclosure.

According to aspects of the disclosure, any of the above-described intraocular stents 20, 120, 220, 220*a*, 320, 320*a*, 420, 520, 620-620*c*, 720 may be ganged up in a stack 800. For example, as shown in FIG. 34, intraocular stent 120 is stacked onto intraocular stent 20 that is in turn stacked onto intraocular stent 220 to form stack 800. As shown in FIG. 34, the inlet port 172 of the central lumen 170 of intraocular stent 120 may be chamfered so that a piercing member 40, 140, 240 and/or a first retainer member 50, 150, 250 of another intraocular stent 20, 120, 220 does/do not get wedged or stuck in the central lumen 170. Inlet port 72 of intraocular stent 20 and inlet port 272 of intraocular stent 220 may be similarly chamfered.

Figure 35:
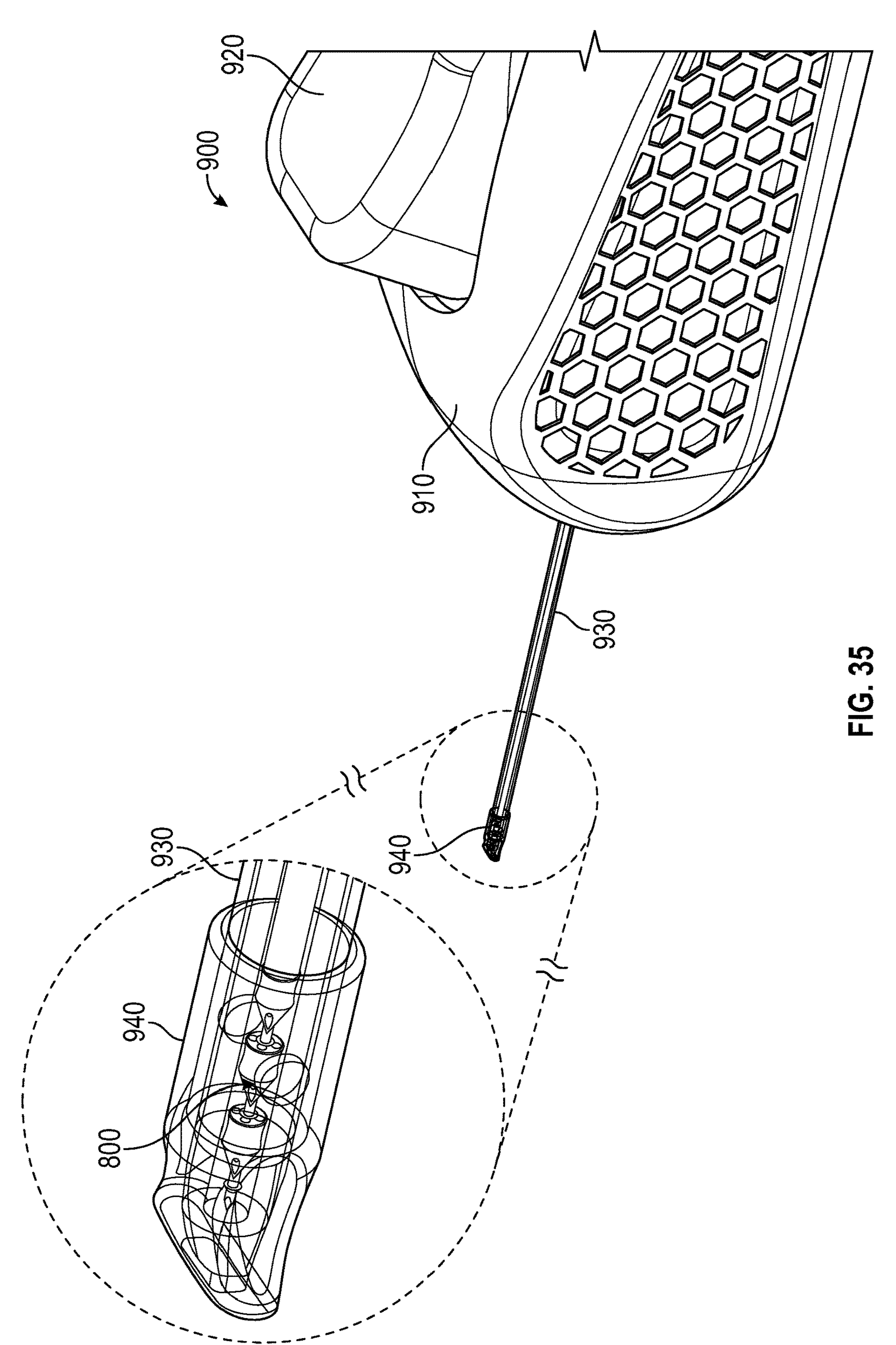
FIG. 35 depicts a perspective view of an intraocular device with the intraocular stent stack of FIG. 34, according to aspects of the disclosure.
Figure 36:
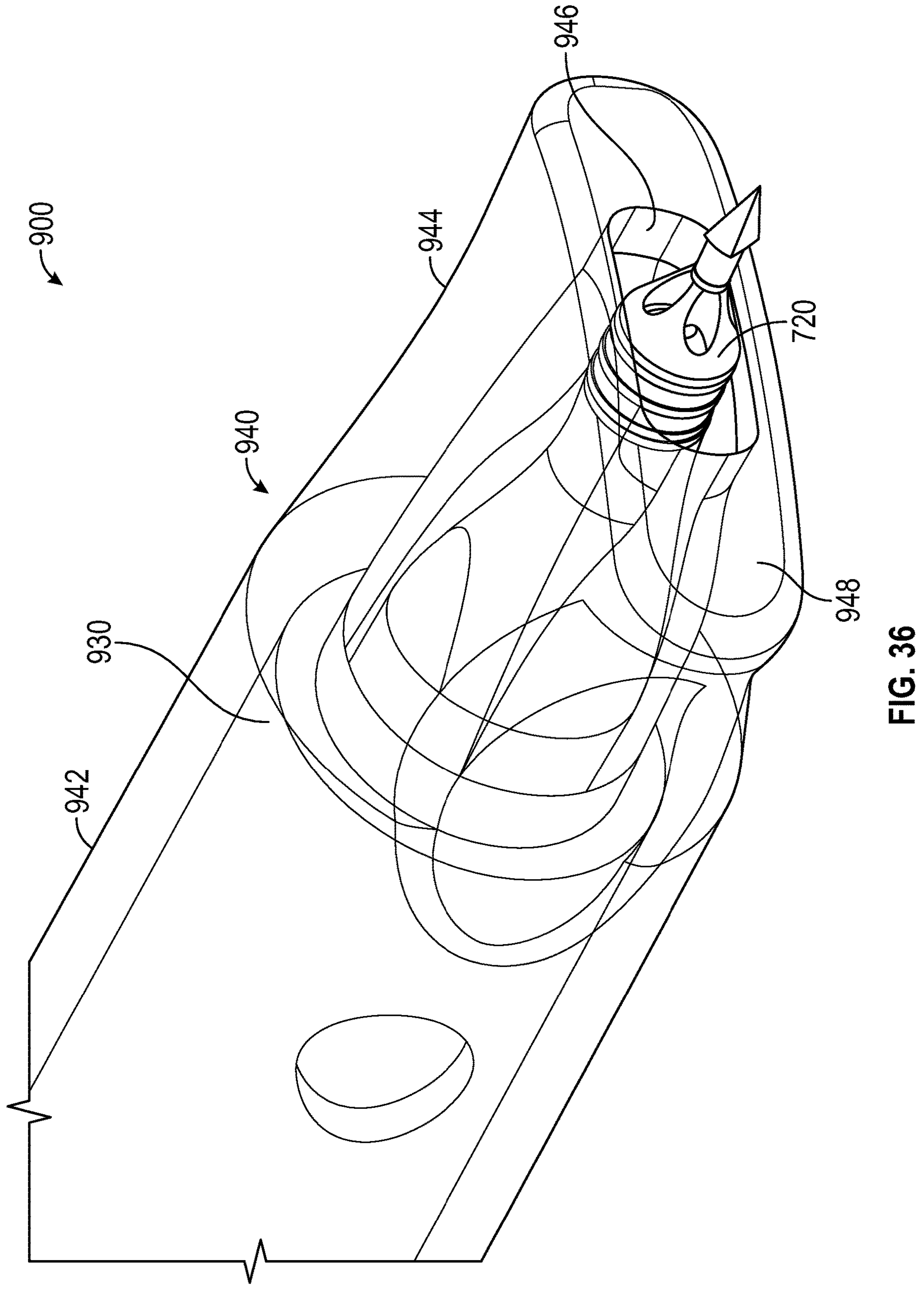
FIG. 36 depicts a partial perspective view of the intraocular device of FIG. 35 with a single intraocular stent, according to aspects of the disclosure.

The stack 800 may then be inserted into a delivery or insertion device such as intraocular device 900 shown in FIG. 35. As shown in FIG. 35, according to aspects of the disclosure, intraocular device 900 may include a handle 910, an activation button 920, a cannula 930 and an insertion tip 940. In use, the insertion tip 940 of the intraocular device 900 may be inserted into the eye and the foremost piercing member (e.g., piercing member 240 of intraocular stent 220) of stack 800 may be pushed into the sclera of the eye by pressing the activation button 920, which may cause the stack 800 to move forward through the cannula 930 and/or may cause the insertion tip 940 to retract backwards relative to the cannula 930.

Thus, the foremost piercing member then penetrates through the trabecular meshwork 94 and through the back wall of the canal of Schlemm (e.g., canal wall 90). The retention member (e.g., retention member 250) of the first stent in the stack 800 may hold the stent (e.g., intraocular stent 220) in place as the insertion tip 940 and cannula 930 of the intraocular device 900 are pulled out of the eye. Here, the piercing member and first retention member (e.g., piercing member 40 and first retention member 50) of the next intraocular stent (e.g., intraocular stent 20) pull free of the inlet port (e.g., inlet port 272) of the implanted intraocular stent 220, thus removing the remainder of stack 800 with the removal of the intraocular device 900.

In aspects of the disclosure, stack 800 may include all of the same intraocular stent (e.g., only intraocular stents 20). In aspects of the disclosure, stack 800 may include any combination of intraocular stents 20, 120, 220, 220*a*, 320, 320*a*, 420, 520, 620-620*c*, 720.

As shown in FIGS. 36-40, the intraocular device 900 may be used to implant a single intraocular stent 20, 120, 220, 220*a*, 320, 320*a*, 420, 520, 620-620*c*, 720 (e.g., intraocular stent 720 is shown). The insertion tip 940 may be a sleeve that is slidably coupled to the cannula 930. The insertion tip 940 may have a cannula portion 942 that is shaped similarly to the shape of the cannula 930 (e.g., circular) and an end portion 944 that may have a different shape (e.g., flared oval) than the cannula portion 942. An opening 946 at the end 948 of the insertion tip 940 may be suitably shaped (e.g., oval) and provide a pathway for the intraocular stent 720 to protrude from. The opening 946 may provide an air pathway that provides for vacuum suction and/or a fluid/debris pathway that provides a passage for fluid or debris being sucked into the intraocular device 900.

Figure 37:
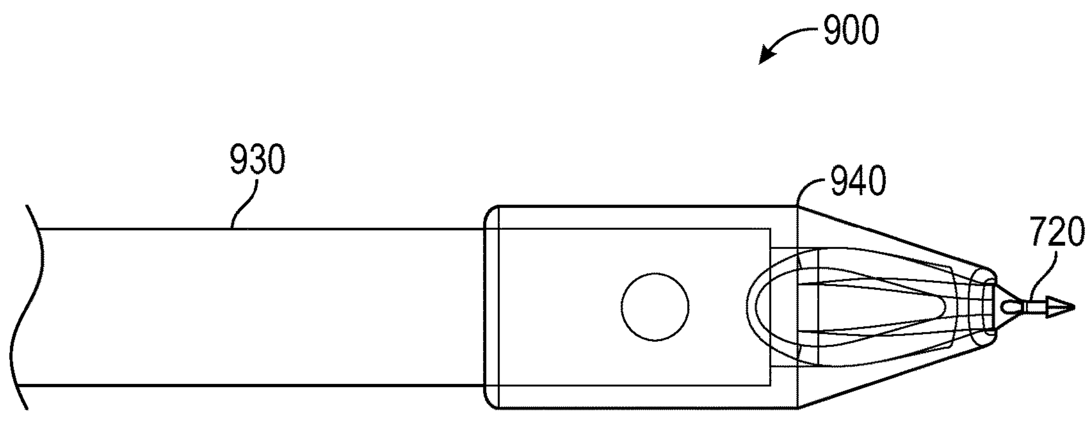
FIG. 37 depicts a partial side view of the intraocular device of FIG. 36 in an inactivated position, according to aspects of the disclosure.
Figure 38:
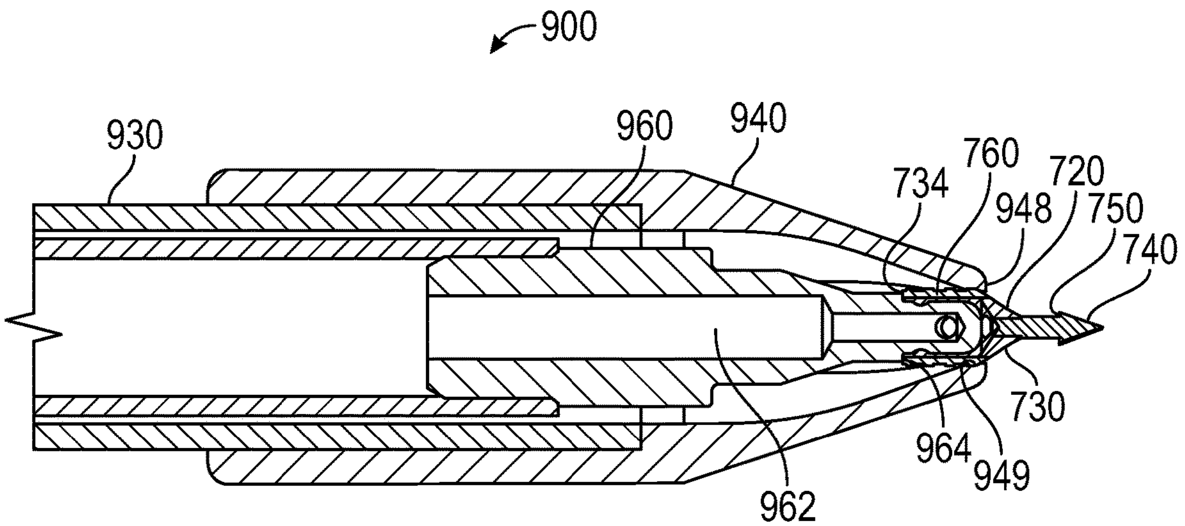
FIG. 38 depicts a cross-sectional side view of the intraocular device of FIG. 37, according to aspects of the disclosure.

As shown in FIGS. 37 and 38, the insertion tip 940 may be disposed in an inactivated position on the cannula 930 with only a portion of the intraocular stent 720 extending past the end 948 of the insertion tip 940. For example, the portion of the housing 730 below the second retention member 760 may protrude from the insertion tip 940 in the inactivated position, such that the piercing member 740 and the first retention member 750 are disposed externally past the insertion tip end 948.

An inserter 960 may be disposed within the cannula 930 and extend out past an end 932 of the cannula 930. The inserter 960 may have a fluid channel 962 configured to allow fluid (e.g., viscous fluid) to flow through the intraocular device 900, into the intraocular stent 720, through the drainage tubes 780 and out into the eye. The inserter 960 may also have a shoulder 964 configured to engage and seal against a top surface 734 of the intraocular stent 720, which may prevent or reduce backflow of fluid through the insertion tip 940 and/or the cannula 930. The shoulder 964 may also provide a surface to push the intraocular stent 720 forward during insertion. In addition, an interior surface 949 of the end 948 of the insertion tip 940 may provide a friction fit with the housing 730 and/or the second retention member 760 of the intraocular stent 720, which may help hold the intraocular stent 720 in place during insertion or injection processes.

Figure 39:
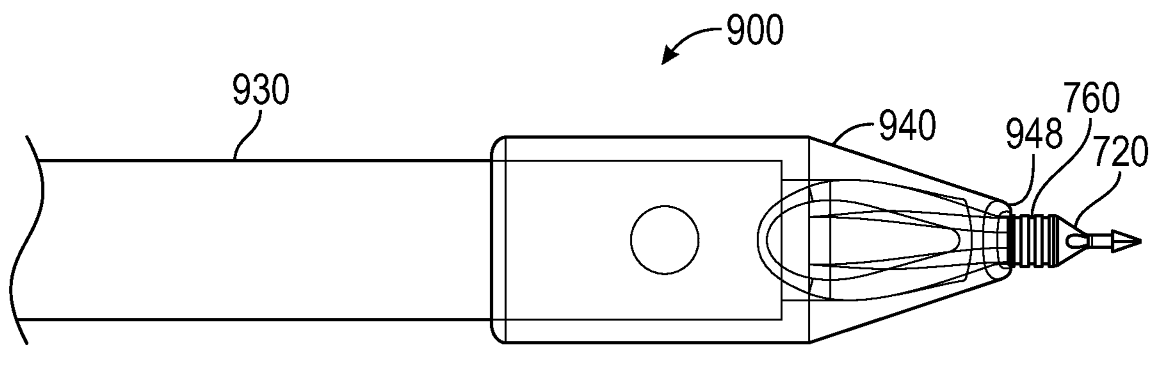
FIG. 39 depicts a partial side view of the intraocular device of FIG. 36 in an activated position, according to aspects of the disclosure.
Figure 40:
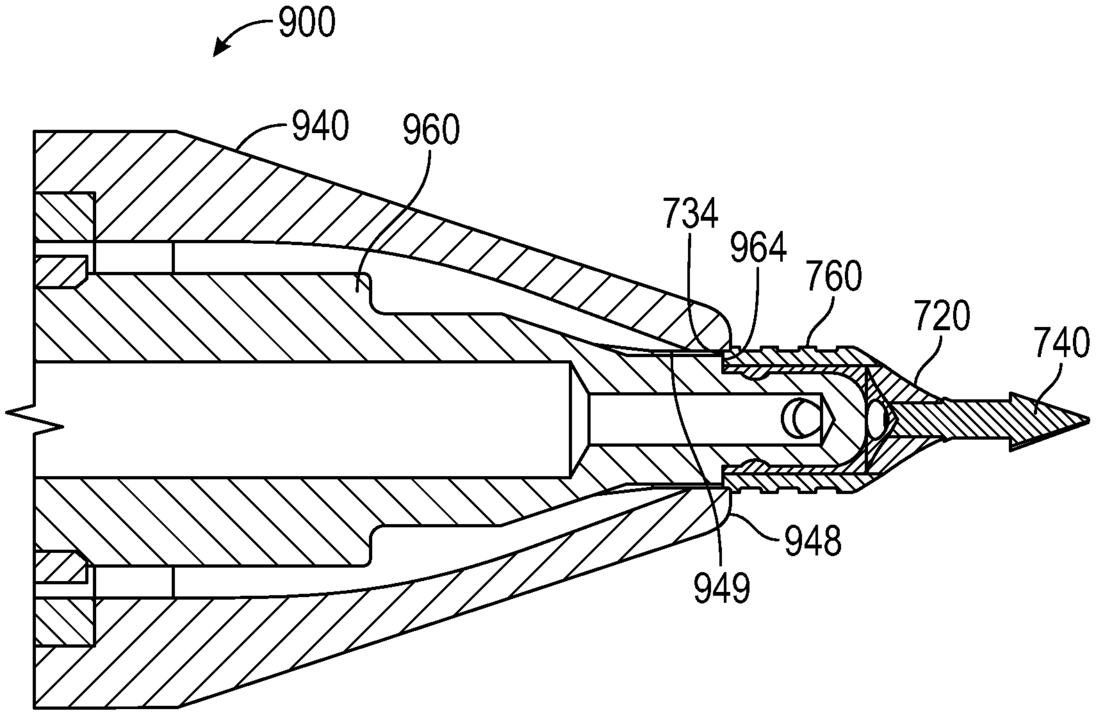
FIG. 40 depicts a cross-sectional side view of the intraocular device of FIG. 39, according to aspects of the disclosure.

As shown in FIGS. 39 and 40, the insertion tip 940 may be disposed in an activated position on the cannula 930 with most or all of the intraocular stent 720 extending past the end 948 of the insertion tip 940. Here, when the intraocular device 900 is triggered from an inactivated position as shown in FIG. 37 to an activated position as shown in FIG. 39, the insertion tip 940 is retracted along the cannula 930 so that the intraocular stent 720 is more fully or totally exposed.

Figure 41:
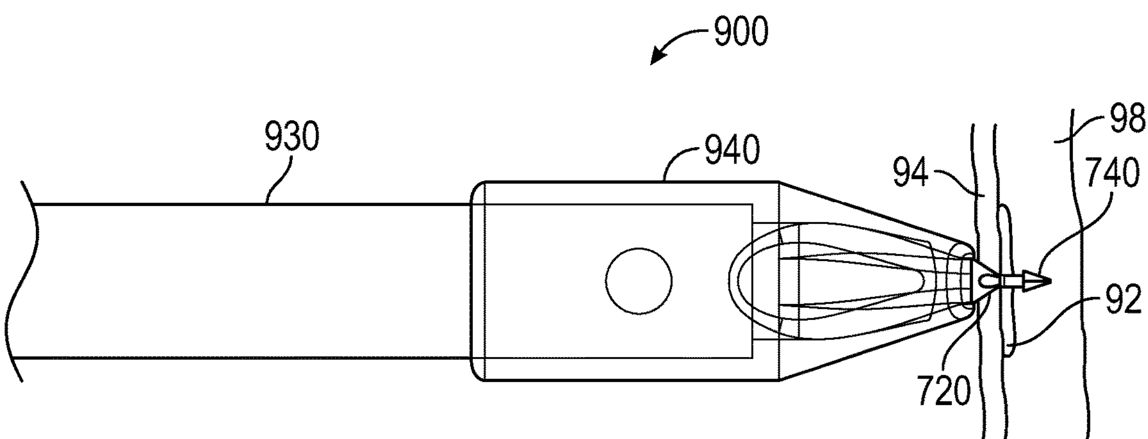
FIG. 41 depicts the partial side view of the intraocular device of FIG. 37 inserted into an eye, according to aspects of the disclosure.
Figure 42:
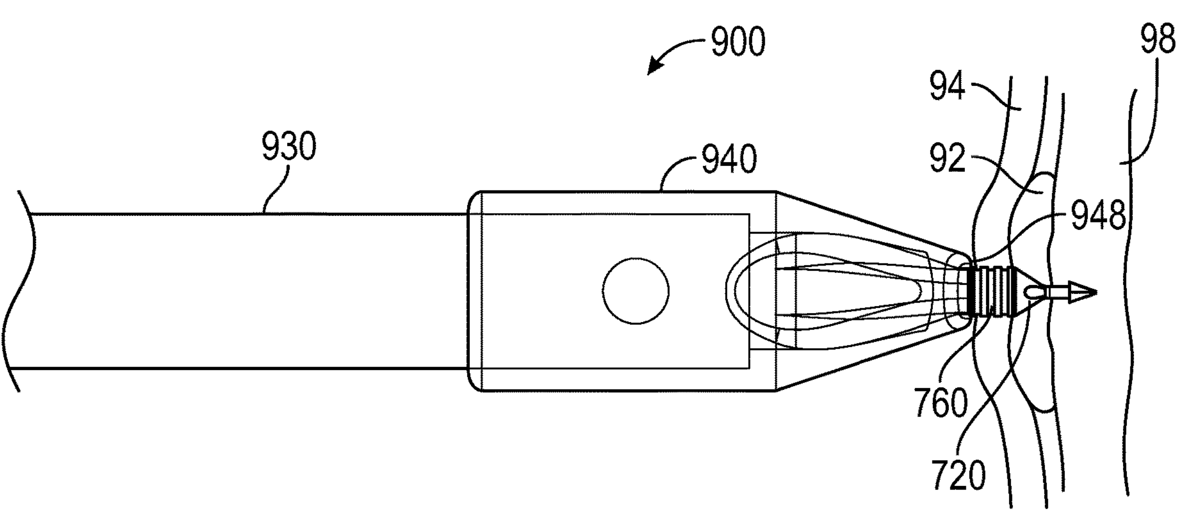
FIG. 42 depicts the partial side view of the intraocular device of FIG. 39 inserted into an eye, according to aspects of the disclosure.
Figures 43, 44, 45:
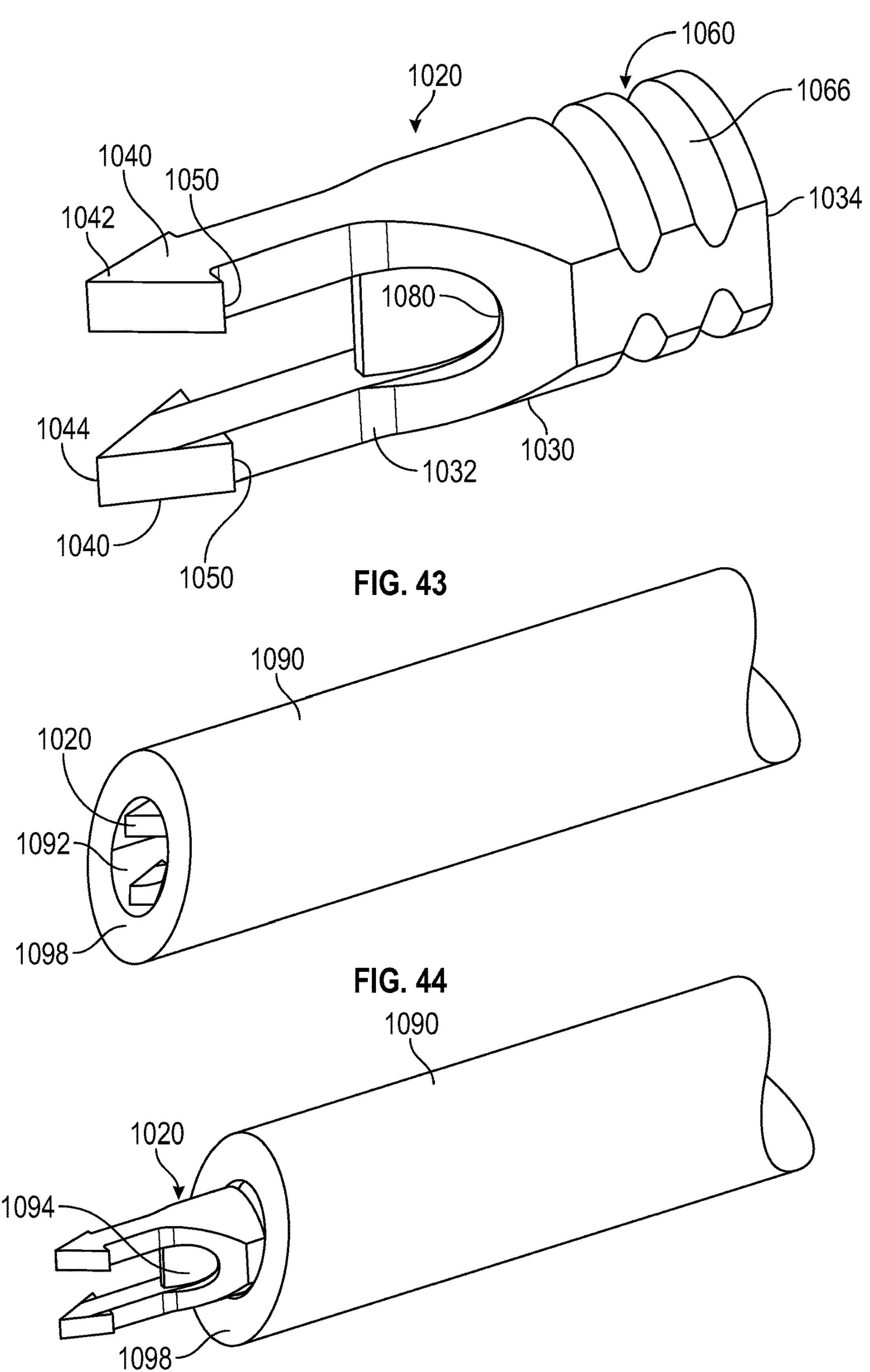
FIG. 43 depicts a perspective view of an intraocular stent, according to aspects of the disclosure.
FIG. 44 depicts a perspective partial view of an intraocular device with the intraocular stent of FIG. 43 in a retracted position, according to aspects of the disclosure.
FIG. 45 depicts a perspective partial view of the intraocular device of FIG. 44 with the intraocular stent in a partially extended position, according to aspects of the disclosure.
Figure 46:
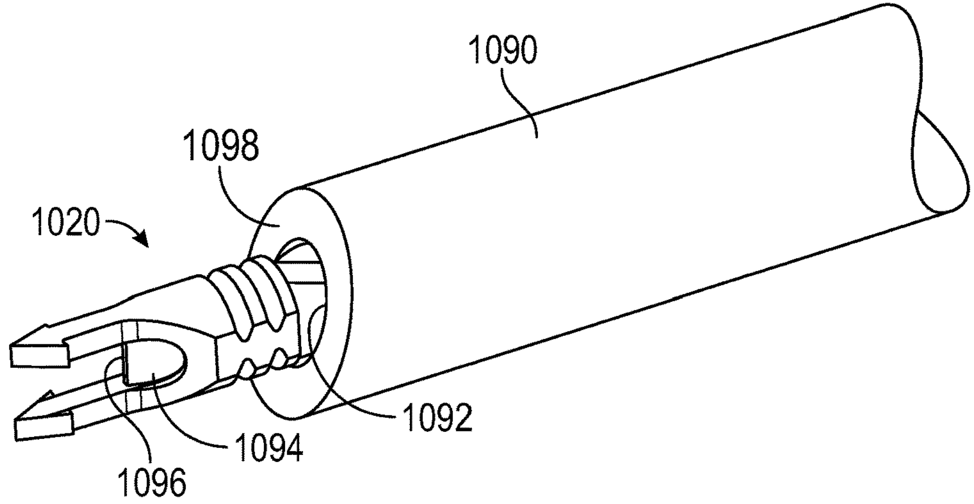
FIG. 46 depicts a perspective partial view of the intraocular device of FIG. 44 with the intraocular stent in an extended position, according to aspects of the disclosure.

For example, as shown in FIG. 41, the intraocular device 900 may be inserted into the eye such that the piercing member 740 of the intraocular stent 720 penetrates through the trabecular meshwork 94 and the canal of Schlemm 92 and into the sclera 98. Here, the end 948 of the insertion tip 940 may be in contact with the outer wall of the trabecular meshwork 94. Once positioned, as shown in FIG. 42, the insertion tip 940 may be retracted and viscous fluid may be injected through the intraocular stent 720 and into the canal of Schlemm 92, causing the canal of Schlemm 92 to expand (e.g., bubble out) from the sclera 98. Here, the second retention member 760 of the intraocular stent 720 may be retained within and/or by the trabecular meshwork 94. The intraocular device 900 may then be removed from the eye, leaving the intraocular stent 720 in place.

As shown in FIGS. 43 to 52, an intraocular stent 1020 may have a housing 1030, piercing members 1040 extending from a bottom portion 1032 of the housing 1030, first retention members 1050 disposed on each piercing member 1040, a second retention member 1060 disposed on the housing 1030, and a lumen 1080 disposed within and through the housing 1030. Like the above-described intraocular stents 20, 120, 220, 220*a*, 320, 320*a*, 420, 520, 620, 620*a*, 620*b*, 620*c*, 720, the intraocular stent 1020 may be inserted and similarly positioned relative to the canal wall 90 of the canal of Schlemm 92 and the trabecular meshwork 94.

The piercing members 1040 may be formed as two barbed portions 1042 that extend parallel to each other from the housing 1030, where the first retention members 1050 are the back ledges of the barbed portions 1042. The second retention member 1060 may be configured similarly to that of second retention member 260. In aspects of the disclosure, the second retention member 1060 may be configured similarly to that of any of the retention members described above. In aspects of the disclosure, the multiple circular channels 1066 provide a depth indication during installation of the intraocular stent 1020.

The intraocular stent 1020 may be configured to be inserted into the eye by an intraocular device (e.g., intraocular device 900) where the intraocular stent 1020 is disposed within a cannula 1090. Here, the cannula 1090 may have a channel 1092 in which the intraocular stent 1020 is slidingly disposed. An insertion trocar 1094 may be inserted through the lumen 1080 of the intraocular stent 1020. For example, an outer diameter of the trocar 1094 may be slightly less than an inner diameter of the lumen 1080. In aspects of the disclosure, the insertion trocar 1094 may have a tip 1096 formed like a chisel, a blade or any other suitable shape. For example, the tip 1096 may be configured to bridge the two piercing members 1040, as shown in FIG. 52.

Figure 47:
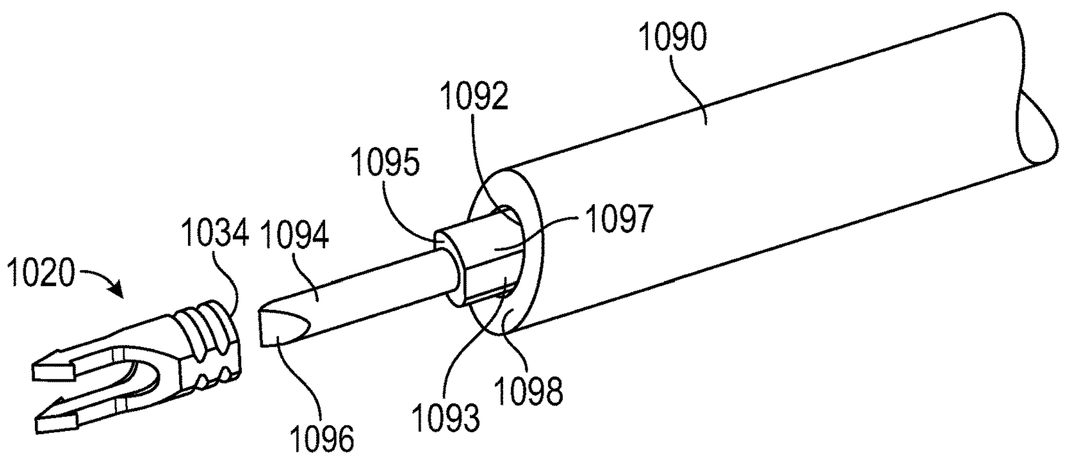
FIG. 47 depicts an exploded perspective partial view of the intraocular device of FIG. 46, according to aspects of the disclosure.

In aspects of the disclosure, the trocar 1094 may be coupled to an end 1095 of a push rod 1097, as shown in FIG. 47. For example, an outer diameter of the end 1095 may be larger than the inner diameter of the lumen 1080 such that the end 1095 may engage with the end 1034 of the intraocular stent 1020, thus providing for the push rod 1097 to slide the intraocular stent 1020 forward out of the cannula 1090 for insertion.

In aspects of the disclosure, the tip 1096 may be positioned where the piercing members 1040 extend from the bottom portion 1032 of the housing 1030 throughout the entire insertion process. For example, the tip 1096 may be positioned this way while the intraocular stent 1020 is inside the cannula 1090 (see FIG. 44) and maintain that position while the intraocular stent 1020 is moved out (e.g., slid out) into the extended position (see FIGS. 45, 46).

Figure 52:
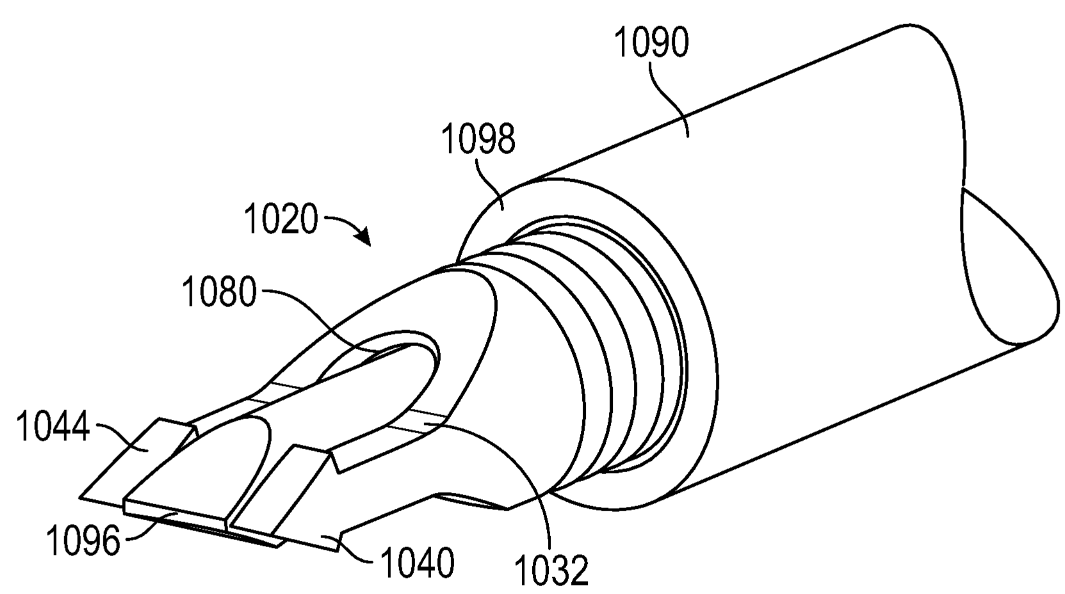
FIG. 52 depicts a perspective partial view of the intraocular device of FIG. 51 with the intraocular stent in an extended position, according to aspects of the disclosure.

In aspects of the disclosure, the tip 1096 may be positioned essentially flush with tips 1044 of the piercing members 1040 while the while the intraocular stent 1020 is inside the cannula 1090 (see FIG. 51) and maintain that position while the intraocular stent 1020 is pushed out into the extended position (see FIG. 52).

In aspects of the disclosure, the tip 1096 may be retracted back towards and/or into the cannula 1090 after the intraocular stent 1020 has been placed in the sclera 98, after which the cannula 1090 may be retracted out of/removed from the eye or placed in a new position within the eye. In aspects of the disclosure, the tip 1096 may maintain its position relative to the piercing members 1040 (e.g., flush with the tips 1044, at the bottom portion 1032 of the housing 1030) when the intraocular stent 1020 has been placed and then the cannula 1090 and tip 1096 may then be removed or moved together while maintaining that relative positioning to each other.

Figure 53:
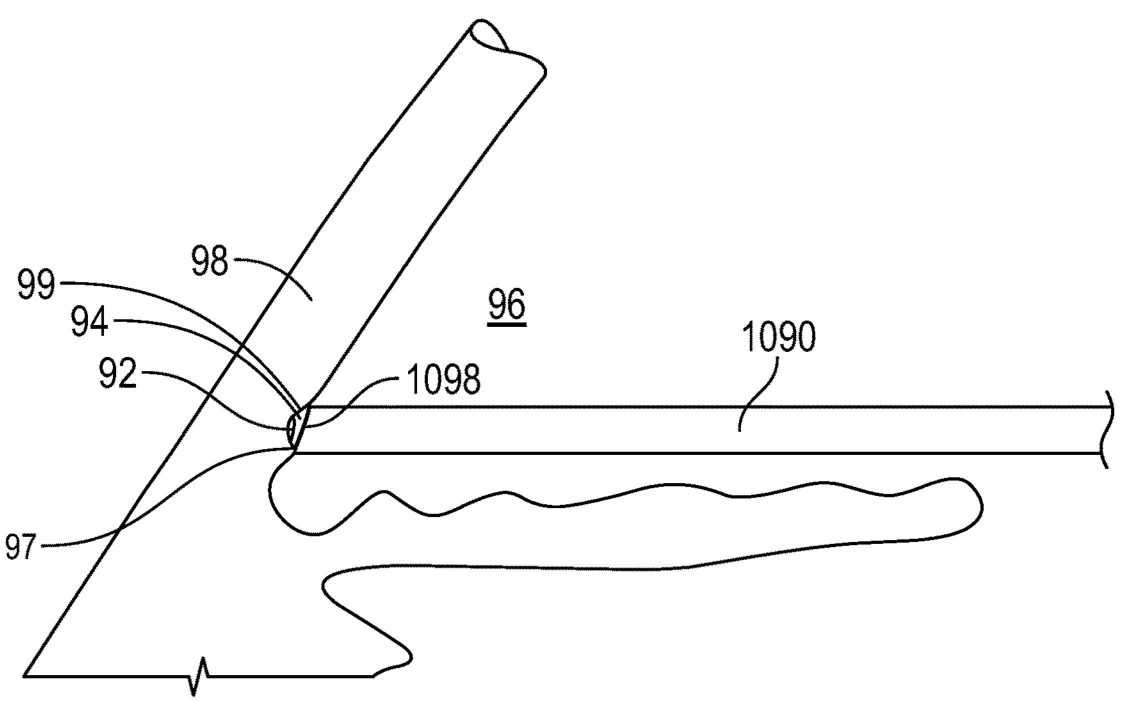
FIG. 53 depicts a schematic view of the intraocular device of FIG. 44 inserted against the sclera of an eye, according to aspects of the disclosure.

In use, according to aspects of the disclosure, the cannula 1090 is inserted into the eye (e.g., through an incision) and maneuvered through the anterior chamber 96 so that the leading end 1098 of the cannula 1090 is adjacent and/or pushed against the sclera 98, in one step. In aspects of the disclosure, the leading end 1098 may be angled as shown in FIG. 53 to line up with an angle of the sclera 98. In aspects of the disclosure, the leading end 1098 is configured to rest against the scleral spur 97 and the Schwalbe's line 99, thus bridging the length of the trabecular meshwork 94 extending between, with the the tip 1096 of the trocar 1094 and the tips 1044 of the piercing members 1040 being aligned while the intraocular stent 1020 is inside the cannula 1090 (see FIG. 51).

Figure 54:
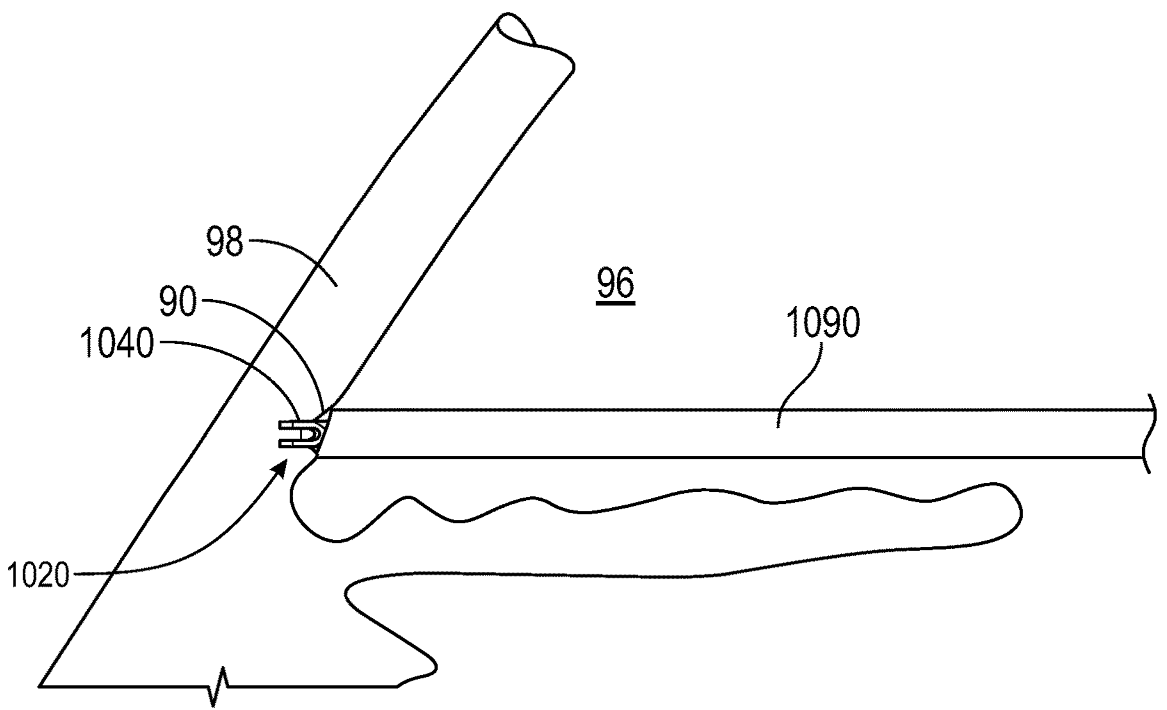
FIG. 54 depicts a schematic view of the intraocular device of FIG. 53 with the intraocular stent in an extended position, according to aspects of the disclosure.

In one step, the trocar 1094 and intraocular stent 1020 are pushed forward to extend out of the cannula 1090 (see FIG. 52) so that the tips 1096 and 1044 penetrate and pass through the trabecular meshwork 94, pass through the canal of Schlemm 92 and engage/push against the wall 90 of the sclera 98. In one step, the trocar 1094 is maintained in position and the intraocular stent 1020 is pushed forward further (see FIG. 46) so that the piercing members 1040 penetrate the wall 90 of the sclera 98 and hold the intraocular stent 1020 in place (see FIG. 54). Here, the first retention members 1050 prevent or minimize movement of the intraocular stent 1020 back out from the wall 90. In one step, the trocar 1094 is retracted back into the cannula 1090, where the tip 1096 of the trocar 1094 may be aligned with the tips 1044 of the next intraocular stent 1020 within the cannula 1090. In one step, the cannula 1090 is withdrawn from the canal of Schlemm 92 and the trabecular meshwork 94, leaving the intraocular stent 1020 in place. In aspects of the disclosure, any of the above-described steps may be combined and/or omitted.

With the intraocular stent 1020 in place, opposing ends of the lumen 1080 are positioned on opposing sides of the trabecular meshwork 94, thus allowing intraocular fluid to flow from the anterior chamber 96, through the lumen 1080 and into the canal of Schlemm 92. In aspects of the disclosure, the intraocular stent 1020 is oriented when deployed through the trabecular meshwork 94 and into the sclera 98 such that space between the two piercing members 1040 provides for fluid to flow along the canal of Schlemm 92.

As described above, a fluid may be injected through the intraocular device (e.g., intraocular device 900) and through the intraocular stent 1020 prior to, during or after being placed in position. For example, a fluid may be injected through the lumen 1080 when the intraocular stent 1020 is within the cannula 1090 in the retracted position and/or once the intraocular stent 1020 is inserted into place in the sclera 98. In addition, fluid may be injected through the cannula 1090 after the cannula 1090 is retracted from the intraocular stent 1020.

Figure 48:
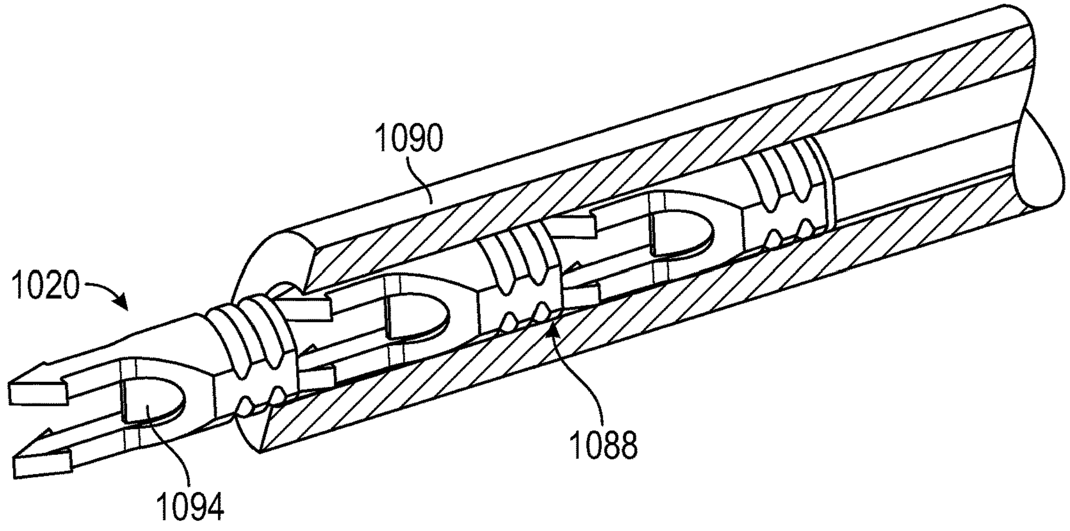
FIG. 48 depicts a cross-sectional perspective partial view of an intraocular device with a stack of intraocular stents, according to aspects of the disclosure.

In aspects of the disclosure, the cannula 1090 may be configured to insert and place a single intraocular stent 1020 at a time. In aspects of the disclosure, the cannula 1090 may be configured to store a stack 1088 of intraocular stents 1020, such as the stack 1088 of three intraocular stents 1020 as shown in FIG. 48. In aspects of the disclosure, intraocular stent 1020 may be mixed with other intraocular stents 20, 120, 220, 220*a*, 320, 320*a*, 420, 520, 620-620*c*, 720 in stack 800.

Figure 49:
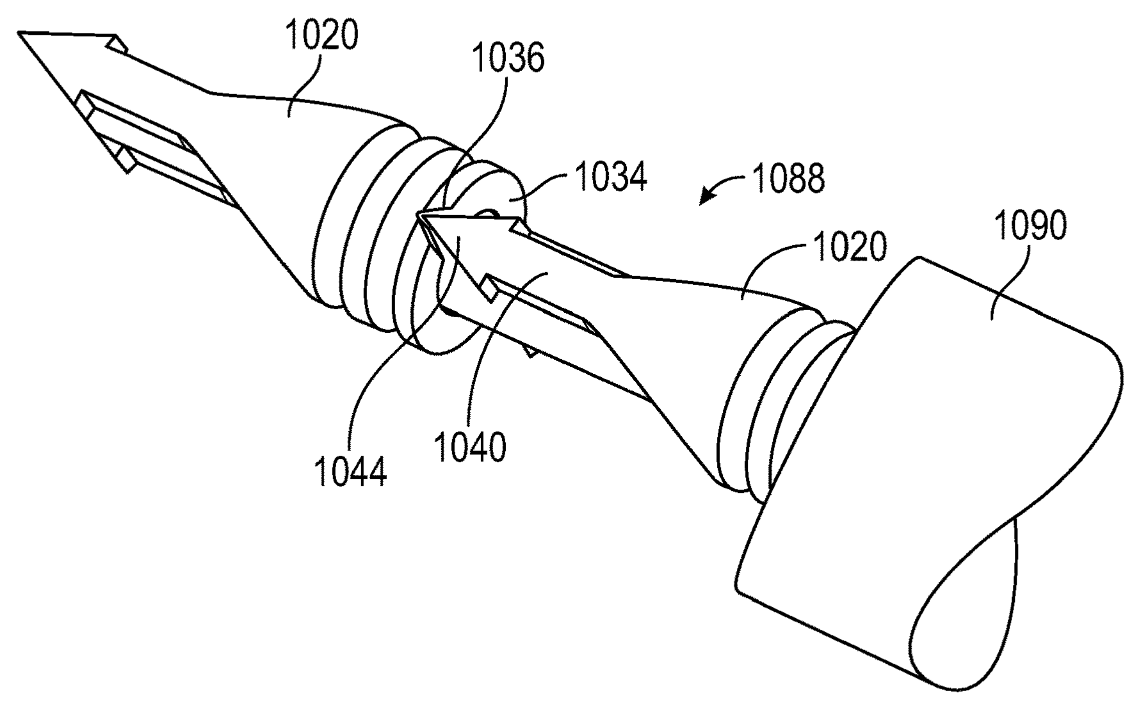
FIG. 49 depicts a perspective partial view of the intraocular device of FIG. 48, according to aspects of the disclosure.

In aspects of the disclosure, one or more keying features may be provided to ensure alignment of the intraocular stent(s) 1020 within the cannula 1090 and during extension of the intraocular stent 1020 out of the cannula 1090. For example, as shown in FIG. 49, the tips 1044 of the piercing member 1040 of an intraocular stent 1020 of stack 1088 may be engaged with or disposed in notches 1036 in an end surface 1034 of the preceding intraocular stent 1020, thus keeping the line of intraocular stents 1020 in the same orientation within the cannula 1090 during storage and use. In aspects of the disclosure, protrusions similar to tips 1044 may extend from the end 1095 of the push rod 1097 in order to mate with the notches 1036 of the innermost intraocular stent 1020.

Figure 50:
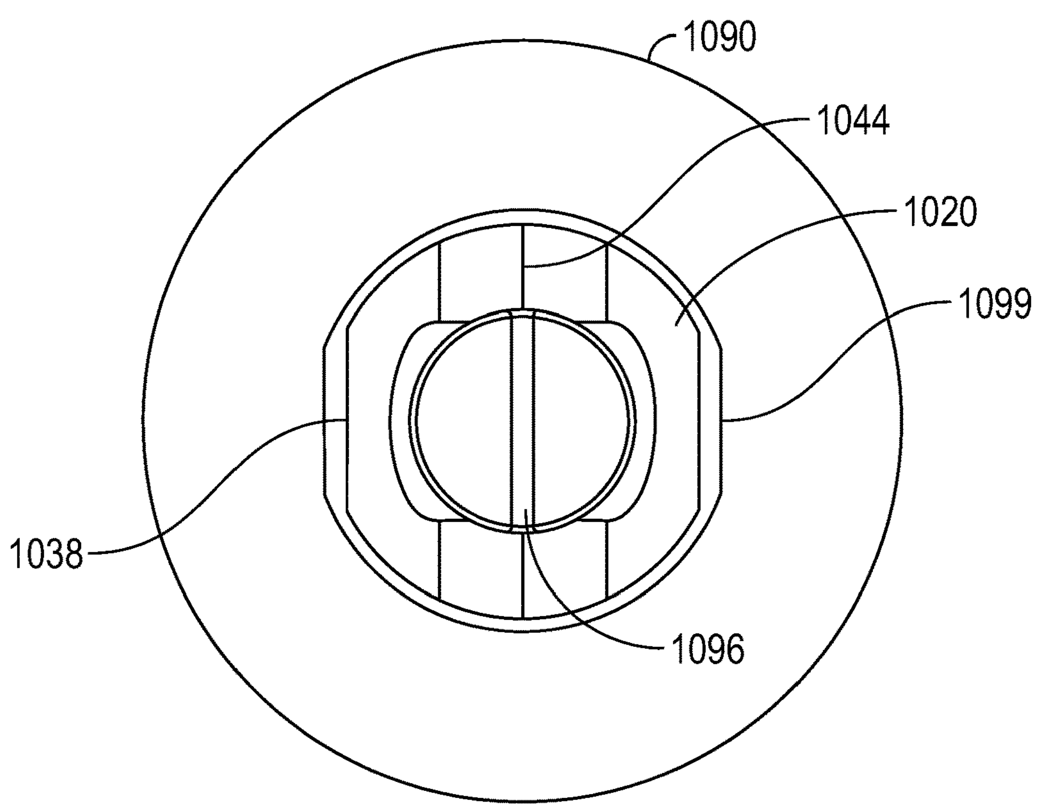
FIG. 50 depicts a front view of an intraocular device with an intraocular stent, according to aspects of the disclosure.
Figure 51:
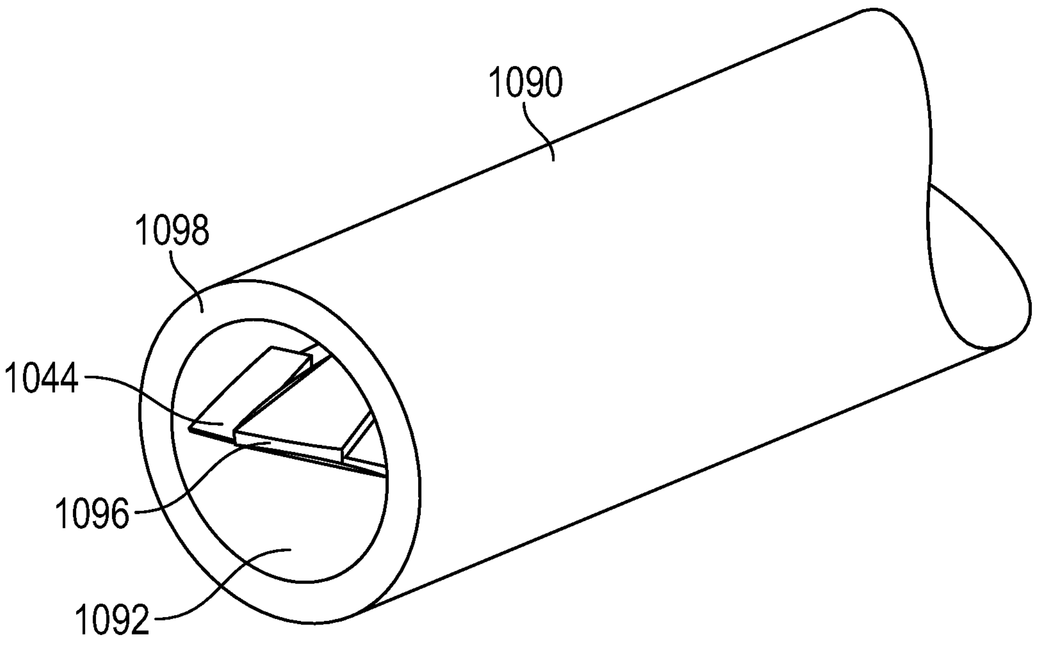
FIG. 51 depicts a perspective partial view of an intraocular device with an intraocular stent in a retracted position, according to aspects of the disclosure.

As shown in FIG. 50, other keying features may include stent keying feature 1038 on the outer diameter of the intraocular stent 1020, which matches up with similar cannula keying feature 1099 on the inner diameter of the cannula 1090, thus keeping the intraocular stent 1020 in a particular alignment within and extending from the cannula 1090. Similarly, as shown in FIG. 47, the outer diameter of the push rod 1097 may include trocar keying feature 1093, which matches up with cannula keying feature 1099 on the inner diameter of the cannula 1090, thus keeping the tip 1096 of the trocar 1094 aligned with the orientation of the tips 1044 of the intraocular stent 1020. In aspects of the disclosure, any combination of the above-described keying features, or any other suitable keying features, may be provided.

In aspects of the disclosure, drug delivery may be provided by any of the above-described intraocular stents 20, 120, 220, 220*a*, 320, 320*a*, 420, 520, 620-620*c*, 720, 1020. For example, a dispenser may be attached or coupled to an anterior portion of the stent so that a drug contained within the dispenser may be dispensed through the stent, such as in one dose or dispensed over time. As another example, a drug may be coated on a portion of the stent (e.g., within the channels 266, 266*a*, 766, 1066) where the coating may biodegrade over time to deliver the drug. In aspects of the disclosure, any portion or feature of the stent may be coated with a drug.

As yet another example, the stent may house an antifibrotic to aide in healing after placement of the stent. For example, the channels 266, 266*a*, 766, 1066 may house any suitable antifibrotic, such as lerdelimumab (CAT-152), Decorin, Suramin, Tranilast, Lovastatin, anaplastic lymphoma kinase (ALK) inhibitor, microRNA, Pegaptanib, Ranibizumab, Bevacizumab, 5D11D4, Y-27932, photodynamic therapy (PDT), Saratin, Sonepcizumab, Doxycycline, Pirfenidone, Tacrolimus, Octreotide, and the like.

In aspects of the disclosure, an ophthalmic viscosurgical device (OVD) or medication may be injected into any of the canal of Schlemm, the trabecular meshwork and collector channels after the stent is released but before it detaches from the inserter. For example, once the stent is in place, the OVD may be injected into the canal of Schlemm and then the stent may be released. In another example, medications may be injected, a dye may be injected, or any other suitable device and/or medication may be injected. For an OVD, the stent may be placed where desired and then the OVD may be injected prior to releasing the stent. This enhances the placement of the OVD by trampolining the trabecular meshwork and creating more space for the intra canal portion, as well as decrease blood reflux in and around the device by blocking blood. In aspects of the disclosure, introducing medication directly into the canal of Schlemm may be used for stem cell therapy localization. In aspects of the disclosure, something may be injected into the layers of the trabecular meshwork (e.g., inject tracer in the layers of trabecular meshwork).

In aspects of the disclosure, injecting anything into the stent may also take place as a secondary step, where the stent is released in place and then a second device engages with the stent to inject OVD, dye (e.g., Trypan Blue), medications, biologics, cells, viral vectors and any other suitable device/medication.

In aspects of the disclosure, one or more sensors may engage with any of the above-described retention features.

In aspects of the disclosure, any of the above-described piercing members (e.g., harpoons) itself may have a lumen that may help drain fluid into the intrascleral space as well as transscleral if the stent is pushed through the entire sclera and the lumen then exists just under Tenon's capsule. This may be a full thickness shunt, but may be implanted so that the distal end of the harpoon is just above the surface of the scleral wall, which may form a bleb in this case.

In aspects of the disclosure, any of the above-describe intraocular stents may be made out of one or more materials that are invisible or partially visible to optical coherence tomography (OCT) wavelengths. In some embodiments, the material of the stent results in minimal artifacts when using OCT imaging. This would allow for OCT assistant implantation of the stent with less reliance on gonioscopy. For example, the stent material(s) may be any of polyvinyl chloride, glycol modified poly (ethylene terephthalate) (PET-G), poly (methyl methacrylate) (PMMA), a polyphenylsulfone, and the like.

According to aspects of the disclosure, any of the above described intraocular stents may be manufactured as a single integral device via a molding process. For example, a single integral device may be manufactured by a molding process in which the intraocular stent is molded as a solid body while using pins to create the central lumen and/or the drainage ports (e.g., two core pins, one from each end, that mate in the middle) or while using fluid dissolvable materials (e.g., dissolvable by water). Once molded, the pins may be removed from the solid body to create the central lumen and/or the drainage ports. As another example, a single integral device may be manufactured by a molding process in which the intraocular stent is molded as a solid body while using fluid dissolvable materials (e.g., dissolvable by water).

Once molded, the device may be immersed in or flushed with dissolving fluid to remove the dissolvable material from the solid body, thus creating the central lumen and/or the drainage ports. As yet another example, a single integral device may be manufactured by a molding process in which the intraocular stent is molded as a solid body and then the central lumen and/or the drainage tubes may be formed by a further process (e.g., drilling, laser etching). In aspects of the disclosure, the central lumen and the drainage tubes may be formed by different methods as described above.

According to aspects of the disclosure, the above described intraocular stents may be manufactured from any suitable materials, including silicon, plastic, polyurethane, acrylic, shape memory plastic and the like.

According to aspects of the disclosure, any of the above described intraocular stents may be surgically implanted in the eye by an ab interno process. The ab interno process may include placing the intraocular stent into a medical instrument (e.g., intraocular device 900), inserting the inserter into the eye and poking the intraocular stent through into the interior of the eye (e.g., the anterior chamber) where a portion of the intraocular stent (e.g., the outlet ports of the intraocular stent) may be disposed in the canal of Schlemm. Thus, the aqueous humor in the anterior chamber may flow into the end of intraocular stent disposed in the anterior chamber and out through the outlet ports positioned on the portion of the intraocular stent disposed in the canal of Schlemm. Normal drainage processes of the eye may then remove the aqueous humor from the canal of Schlemm.

It is understood that any specific order or hierarchy of blocks in the methods of processes disclosed is an illustration of example approaches. Based upon design or implementation preferences, it is understood that the specific order or hierarchy of blocks in the processes may be rearranged, or that all illustrated blocks be performed. In some implementations, any of the blocks may be performed simultaneously.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

As used herein, the phrase "at least one of" preceding a series of items, with the term "or" to separate any of the items, modifies the list as a whole, rather than each item of the list. The phrase "at least one of" does not require selection of at least one item; rather, the phrase allows a meaning that includes at least one of any one of the items, and/or at least one of any combination of the items, and/or at least one of each of the items. By way of example, the phrase "at least one of A, B, or C" may refer to: only A, only B, or only C; or any combination of A, B, and C.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that the specific order or hierarchy of steps, operations or processes disclosed is an illustration of exemplary approaches. Based upon design preferences, it is understood that the specific order or hierarchy of steps, operations or processes may be rearranged. Some of the steps, operations or processes may be performed simultaneously. Some or all of the steps, operations, or processes may be performed automatically, without the intervention of a user. The accompanying method claims, if any, present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112 (f) unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but are to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. An intraocular stent, comprising:

a housing having a first portion and a second portion;

a piercing member extending from the second portion of the housing;

a first retention member disposed on the piercing member;

a second retention member disposed on the first portion of the housing;

a central lumen disposed within the housing; and one or more drainage tubes disposed within the housing, wherein the second retention member comprises one of:

a curved sidewall such that the first portion of the housing comprises an hourglass shape; and a chamfered sidewall such that the first portion of the housing comprises a trapezoidal shape, and wherein the second retention member has a narrow central portion and a wide end portion, wherein the wide end portion is configured to be disposed in an anterior chamber of an eye and the narrow central portion is configured to be engaged with a trabecular meshwork of the eye.

2. The intraocular stent of claim 1, wherein a leading end of the piercing member comprises a pointed spike.

3. The intraocular stent of claim 1, wherein the first retention member comprises a chamfered sidewall having a sloped surface with a narrow portion of the sloped surface disposed closer to a leading end of the piercing member and a wide portion of the sloped surface disposed closer to the housing.

4. The intraocular stent of claim 3, wherein a widest portion of the chamfered sidewall comprises a flange surface configured to engage with a wall of a canal of Schlemm of an eye.

5. The intraocular stent of claim 1, wherein the second retention member comprises one or more circular protrusions extending radially from the first portion of the housing, wherein one of the one or more circular protrusions is configured to be engaged with a trabecular meshwork of an eye.

6. The intraocular stent of claim 1, wherein the central lumen is disposed axially within the housing, the central lumen having an inlet port disposed on a first end of the first portion of the housing, the central lumen extending through the first portion of the housing and into the second portion of the housing.

7. The intraocular stent of claim 6, wherein the one or more drainage tubes are disposed within the second portion of the housing and coupled to the central lumen, each drainage tube having an outlet port disposed on an outer surface of the second portion of the housing.

8. The intraocular stent of claim 7, wherein the one or more drainage tubes are orthogonally coupled to the central lumen.

9. The intraocular stent of claim 7, wherein the one or more drainage tubes are coupled to the central lumen at an angle greater than 90 degrees.

10. The intraocular stent of claim 6, wherein the one or more drainage tubes are disposed axially within the housing and parallel to the central lumen, each drainage tube having an inlet port disposed on the first end of the first portion of the housing and an outlet port disposed on an outer surface of the second portion of the housing.

11. The intraocular stent of claim 10, wherein the one or more drainage tubes intersect with the central lumen to form a unified fluid pathway for a length of the central lumen.

12. The intraocular stent of claim 6, wherein the one or more drainage tubes are disposed within the housing at an angle to the central lumen, each drainage tube having an inlet port disposed on the first end of the first portion of the housing and an outlet port disposed on an outer surface of the second portion of the housing.

13. The intraocular stent of claim 12, wherein a portion of the one or more drainage tubes intersect with the central lumen.

14. An intraocular stent, comprising:

a housing having a first portion and a second portion;

a piercing member extending from the second portion of the housing;

a first retention member disposed on the piercing member;

a second retention member disposed on the first portion of the housing; and a plurality of drainage tubes disposed within the housing, wherein the plurality of drainage tubes are linear and disposed at an angle within the housing, each drainage tube having an inlet port disposed on a first end of the first portion of the housing and an outlet port disposed on an outer surface of the second portion of the housing.

15. The intraocular stent of claim 14, wherein a flange surface of the first retention member is configured to engage with a wall of a canal of Schlemm of an eye, wherein a portion of the second retention member is configured to be engaged with a trabecular meshwork of the eye, and wherein an end portion of the first portion of the housing is configured to be disposed within an anterior chamber of the eye.

16. A plurality of intraocular stents, each intraocular stent, comprising:

a housing having a first portion and a second portion;

a piercing member extending from the second portion of the housing;

a first retention member disposed on the piercing member;

a second retention member disposed on the first portion of the housing;

a central lumen disposed within the housing, the central lumen having a chamfered inlet port disposed on a top surface of the first portion of the housing; and one or more drainage tubes disposed within the housing, wherein the plurality of intraocular stents are configured to be stacked together, wherein the piercing member and the first retention member of a first intraocular stent are disposed in the central lumen and the chamfered inlet port respectively of a second intraocular stent.

* * * * *